(12) United States Patent
Luo et al.

(10) Patent No.: US 7,078,485 B2
(45) Date of Patent: Jul. 18, 2006

(54) N-TERMINAL MODIFIED RECOMBINANT HUMAN ENDOSTATIN AND ITS PRODUCTION

(75) Inventors: Yongzhang Luo, Yantai (CN); Bing Zhou, Yantai (CN); Zhuobing Zhang, Yantai (CN)

(73) Assignee: Yantai Medgenn Ltd. (CN)

( * ) Notice: Subject to any disclaimer, the term of this patent is extended or adjusted under 35 U.S.C. 154(b) by 291 days.

(21) Appl. No.: 10/313,638

(22) Filed: Dec. 5, 2002

(65) Prior Publication Data

US 2004/0110671 A1 Jun. 10, 2004

(51) Int. Cl.
C07K 1/00 (2006.01)
A61K 61/00 (2006.01)
C12P 21/06 (2006.01)

(52) U.S. Cl. .................. 530/350; 435/69.1; 514/12
(58) Field of Classification Search ............ 514/2, 514/12; 435/69.1; 530/300, 350
See application file for complete search history.

(56) References Cited

U.S. PATENT DOCUMENTS 6,551,840 B1 * 4/2003 Ono et al. ............... 436/501
2004/0229338 A1 * 11/2004 King .................. 435/252.3

FOREIGN PATENT DOCUMENTS

CN        00107569.1      12/2001
WO        00/48622   *    8/2000

OTHER PUBLICATIONS

B. Kim Lee Sim et al., Zinc ligand-disrupted recombinant human Endostatin: Potent inhibition of tumor growth, safety and pharmokinetic profile, Angiogenesis, 1999, 41-51, Netherlands.
Noriko Yamaguchi et al., Endostatin inhibits VEGF-induced endothelial cell migration and tumor growth indeoendently of zinc binding, The EMBO Journal, 1999, 18(16):4414-4423.
Michael S. O'Reilly et al., Endostatin: An Endogenous Inhibitor of Angiogenesis and Tumor Growth, Cell, Jan. 24, 1997, 88:277-285.
Erhard Hohenester et al., Crystal Structure of the angiogenesis inhibitor endostatin at 1.5 Å resolution, The EMBO Journal, 1998, 17(6):1656-1664.
Yuan-Hua Ding et al., Zinc dependent dimers observed in crystals of human endostatin, Proc. Natl. Acad, Sci. USA, Sep. 1998, 95:10443-10448.
Thomas Boehm et al., Zinc-Binding of Endostatin id Essential for Its Antiangiogenic Activity, Biochemical and Biophysical Research Communications, 1998, 252:190-194.
Mohanraj Dhanabal et al., Cloning, Expression and *in Vitro* Activity of Human Endostatin, Biochemical and Biophysical Research Communications, 1999, 258: 345-352.
Mohanraj Dhanabal et al., Endostatin: Yeast Production, Mutants, and Antitumor Effect in Renal Cell Carcinoma, Cancer Research, 1999, 59: 189-197.
Erhard Hohenester et al., Crystal structure of the angiogenesis inhibitor endostatin at 1.5 Å resolution, The EMBO Journal, 1998, 17(6): 1656-1664.
Judah Folkman, Clinical Applications of Research on Angiogenesis, Seminars in Medicine of the Beth Israel Hospital., Boston, 1995, 333(26): 1757-1763.
Judah Folkman and Yuen Shing, Angiogenesis, The Journal of Biological Chemistry, 1992, 267(16): 10931-10934.
Thomas Boehm et al, Antiangiogenic therapy of experimental cancer does not induce acquired drug resistance, Letters to Nature, 1997, 390: 404-407.

* cited by examiner

*Primary Examiner*—Maryam Monshipouri
(74) *Attorney, Agent, or Firm*—Saliwanchik, Lloyd & Saliwanchik

(57) ABSTRACT

The invention relates to endostatin protein, in particular, to N-terminal modified recombinant human endostatin (rhEndostatin) proteins which have an additional metal chelating peptide sequence at the N-terminal, the preparation thereof, and methods of modifying the rhEndostatin to improve its stability in vivo and in vitro, and its biological activity. The invention further related to the resulting N-terminal modified rhEndostatin protein, a pharmaceutical composition containing the same, and use of said modified rhEndostatin or its pharmaceutical composition in treating the angiogenesis-related diseases, especially angiogenesis-dependent tumors.

12 Claims, 15 Drawing Sheets

FIGURE 6A
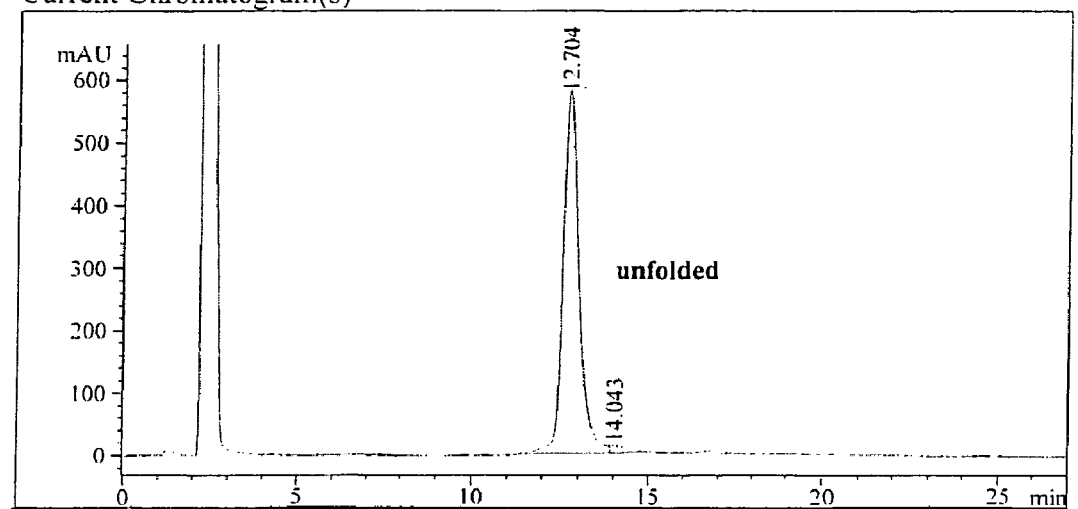
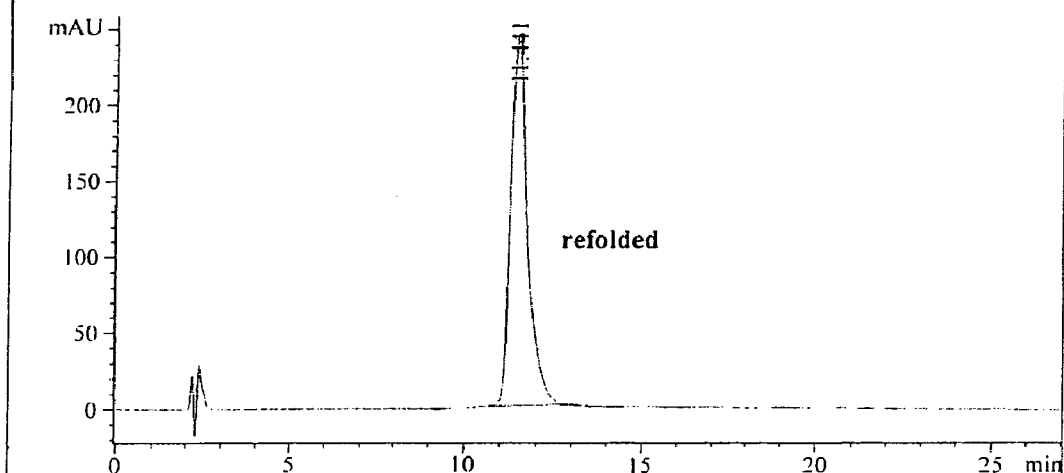
FIGURE 6B

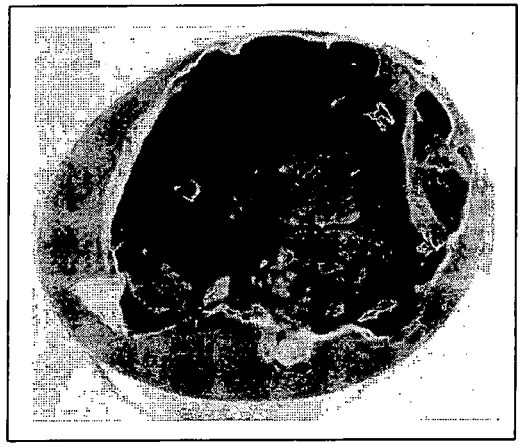 
FIGURE 12A　　　　　　　　FIGURE 12B
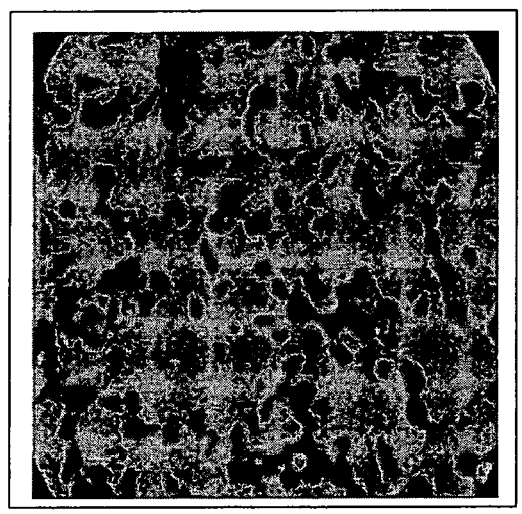 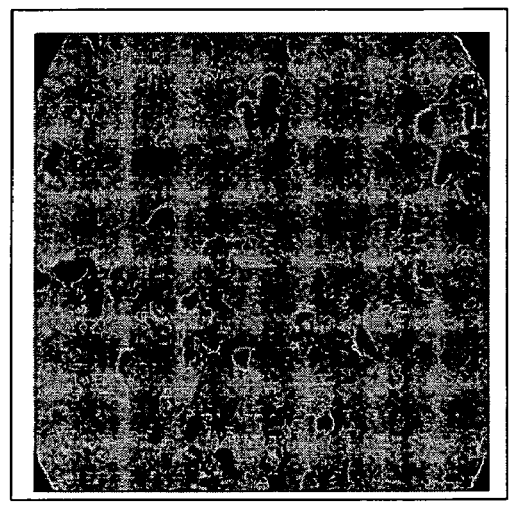
FIGURE 13A　　　　　　　　FIGURE 13B

N-TERMINAL MODIFIED RECOMBINANT HUMAN ENDOSTATIN AND ITS PRODUCTION

FIELD OF THE INVENTION

The invention is generally related to endostatin protein, in particular, to N-terminal modified recombinant human endostatin (rhEndostatin) protein which have a additional metal chelating peptide sequence at the N-terminal, the preparation thereof and a method of modifying the rhEndostatin to improve its stability in vivo and in vitro, and its biological activity. The invention further relates to the resulting N-terminal modified rhEndostatin protein, a pharmaceutical composition containing the same, and use of said modified rhEndostatin or its pharmaceutical composition in treating the angiogenesis-related diseases, especially angiogenesis-dependent tumors.

BACKGROUND OF THE INVENTION

Angiogenesis, the process of new blood vessel development and formation, plays an important role in numerous physiological events, both normal and pathological. Angiogenesis occurs in response to specific signals and involves a complex process characterized by infiltration of the basal lamina by vascular endothelial cells in response to angiogenic growth signal(s), migration of the endothelial cells toward the source of the signal(s), and subsequent proliferation and formation of the capillary tube. Blood flow through the newly formed capillary is initiated after the endothelial cells come into contact and connect with a preexisting capillary.

Angiogenesis is indispensable for embryonic development, organogenesis, tissue regeneration and repair, wound healing and female reproductive processes (Folkman, J. And Shing, Y., J. Biol. Chem. 267:109931–10934, 1992; Folkman, J., Nature Medicine 1: 27–31, 1995). Meanwhile, angiogenesis is also one of the necessary factors that cause the progression and deterioration of many pathological disorders including cancer growth and metastasis, cardiovascular disease, diabetic retinopathy, rheumatoid arthritis, etc. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis.

Angiogenesis is a complex multi-stage process that includes proliferation, migration and differentiation of endothelial cells, proteolytic degradation of the basement membrane, differentiation and migration of endothelial cells into the surrounding stroma, and finally formation of vasculature and new capillaries. The naturally occurring balance between endogenous stimulators and inhibitors of angiogenesis is one in which inhibitory influences predominate (Rastinejad et al., 1989, Cell 56:345–355).

Angiogenesis stimulators that can be mentioned include vascular endothelial growth factor (VEGF), vascular permeability factor (VPF), fibroblast growth factor (FGF-1 and -2), etc. On the other hand, some angiogenesis inhibitors have also been found and identified recently, which includes a 29 KDa fragment of fibronectin, thrombospondin (TSP-1), platelet factor 4, a 16 KDa fragment of prolactin, and a 38 KDa fragment of plasminogen and the like. In particular, recently O'Reilly et al. identified and characterized an internal 38 KDa fragment of plasminogen as angiostatin and a 20 KDa globular C-terminal of collagen XVIII as endostatin. It is suggested based on the current research results that the angiogenesis phenotype in the tissue depends on the dynamic equilibrium of angiogenesis stimulator and inhibitors in the local tissue environment (Folkman, J., N. Engl. J. Med. 333: 1757–1763, 1995).

Particularly interesting is that recent research shows that most angiogenesis inhibitors as mentioned above display the inhibitory activity of endothelial cell proliferation only after their parent proteins are hydrolized and form terminal or internal fragments. Thus, it is suggested that protein hydrolysis by endogenous peptidases plays a key role in the expression of their biological activities (O'Reilly, M. S. et al., Cell 88:277–285, 1997).

As a 20 KDa carboxyl terminal fragment of collagen XVIII, endostatin is a special inhibitor of endothelial cell proliferation and migration, and it also markedly inhibits the growth of many kinds of cancers (O'Reilly, M. S. et al., Cell 88:277–285, 1997; U.S. Pat. No. 5,854,205). It was shown that repeated endostatin administration leads to prolonged stable state of mice cancers, and there was no induction of drug resistance (Boehm, T. et al., Nature 390:404–407, 1997). It was further shown that endostatin causes cells to be quiescent at cell cycle G1 phase and specifically induces apoptosis of endothelial cells (Dhanabalk, M. et al., Biochem. Biophys. Res. Commun. 258: 345–352, 1999).

Endostatin was initially isolated from a hemangioendothelioma cell line for its ability to inhibit the proliferation of capillary endothelial cells (O'Reilly, M. S. et al., Cell 88:277–285, 1997). Based on the analysis of its nucleotide sequence, O'Reilly et al. further expressed endostatin protein in an *E. coli* expression system in un-refolded form, and it is believed that the unfolded purified protein facilitates its prolonged release at the subcutaneous injection site. The authors also mentioned that when endostatin was refolded by a standard method and solublized into tissue culture media, it strongly inhibited the proliferation of endothelial cells. Unfortunately, about 99% of protein was lost during protein refolding. In addition, though it has been reported that protein having anti-angiogenesis activity can be expressed in prokaryotes, the product can hardly refold into soluble form and tends to precipitate out of the solution. Further, cloning and expressing soluble recombinant endostatin in a yeast (*Pichia pastoris*) system were also reported (see, for example, Dhanabal, M. Et al., Cancer Res. 59: 189–197, 1999).

Yuan-Hua Ding and his co-workers (Yuan-Hua Ding et al., *Proc. Natl. Acad. Sci. USA* 95,10443–10448, 1998) revealed a zinc-binding site in the structure analysis of human endostatin by x-ray crystallography, and supposed that the zinc site could be involved either in the cleavage of the precursor or in some activity following cleavage. The writers concluded that "strategies for stabilizing the zinc-binding loop with other metals may be useful to stabilize the protein, especially if the loop contacts a receptor. Protein engineering to create a convalent dimer by a disulfide link or by forming a single chain dimer based on the proximity of the C and N termini of respective monomers, might produce a more potent protein." Also, the previous study by Boehm et al. (Boehm, T. et al., Biochem. Biophys. Res. Commun., 252:190–194,1998 ) suggested that zinc-binding is essential for the angiogenesis activity of endostatin.

However, contrary to the conclusion of the studies discussed above, B. K. L. Sim and his co-workers (B. Kim Lee Sim et al., *Angiogenesis* 3,41–51,1999 ) have shown that deletion of two (His1 and His3) of the four zinc ligands of recombinant human (rh) Endostatin did not affect the inhibitory activity of the protein in vivo. However, for these completely different results, the writers did not give a satisfactory explanation.

Furthermore, Sim et al. demonstrated soluble and unrefolded rhEndostatin produced in *P. pastoris* exhibits an inhibition of 40–98% in the B16-BL6 metastatic tumor model, but the effective inhibitory dose up to 50 mg/kg/12 h. Additionally, it has been shown that (2001, 2002 ASCO Annual Meeting Report: www.entremed.com) the effective amount of endostatin expressed in yeast system is astonishingly about 240–600 mg/m$^2$/person in recent clinical trials. Obviously, such a high dose must have a great stress on large scale manufacture for clinical trials and on industrial production in the future, even though it appears safe in high doses as determined in mouse and monkeys. Also, to reduce the dosage and to increase the effect, continuous infusion with pumps has been tried in their clinical trials. However, this will make the patients suffer a great inconvenience, and it does not lead to an obviously improved effect.

Because of the huge dosage of endostatin used as cancer growth inhibitor in the preclinical and clinical studies, in addition to the problem of being difficult to refold and easy to precipitate for product expressed in *E. coli*, secreted recombinant human endostatin that is expressed in a yeast expression system is currently preferred. But use of the yeast system demands huge amount of investment (for example up to 10 or more tons of fermentor), long production cycles, and suffers the danger of huge losses incurred by possible contamination.

Due to the problems existing in the practical application for recombinant human endostatin, it is necessary to seek a new production method and product that has higher yield, low cost, and better in vivo stability in order to improve the clinical effects of recombinant human endostatin in the treatment of cancers or other angiogenesis related diseases.

China Patent No. 00107569.1 (its publication date is Dec. 5, 2001) described endostatin with elongated N-terminal or additional amino acids at the N-terminal, and a method for production in prokaryotes (*E. coli*, for example) expression system. The human endostatin with additional amino acids at the N-terminal is produced in refolded form in high yield, thereby supporting large scale manufacture for clinical evaluation. Recently, on the basis of our previous experimental research, our further pharmacological and pharmacokinetics studies showed that human endostatin with N-terminal additional amino acid sequence as disclosed in China Patent No. 00107569.1 has better in vivo stability and biological activity than our previously produced native endostatin in yeast, thereby markedly improving its pharmaceutical activity and substantially decreasing the clinical administration doses. These findings and improvements of the present inventors provide the desirability and availability of the modified rhEndostatin protein for the use in clinical practices.

OBJECTS OF THE INVENTION

Accordingly, one object of the present invention is to provide a modified recombinant human endostatin (rhEndostatin), wherein the N-terminal of the recombinant endostatin carries an additional metal chelating peptide sequence.

In one preferred embodiment, the modified endostatin with additional metal chelating peptide at the N-terminal has the following general formula:

(Xaa)m(His)n-endo wherein Xaa represents any neutral amino acid residue, and m is integer of 0–4; n is integer of 2–8, and any two consecutive histidines residues may be separated by one or two non-histidine residues; and -endo represents native endostatin sequence.

In another preferred embodiment, said N-terminal additional metal chelating peptide has the following amino acid sequence:

MetGlyGlySerHisHisHisHisHis (SEQ ID NO:1)

In a further preferred embodiment, the sequence of the first 15 N-terminal amino acids of the modified endostatin with additional metal chelating peptide at its N-terminal is as follows:

MetGlyGlySerHisHisHisHisHisSerHisArgAspPhe (SEQ ID NO:2)

It is another object of the present invention to provide a method for modifying native recombinant endostatin to improve its in vivo stability and biological activity, said method includes modifying the DNA coding sequence of the native recombinant endostatin protein and adding an additional metal chelating peptide at its N-terminal.

In one preferred embodiment, the endostatin with additional metal chelating peptide at the N-terminal has the following general formula:

(Xaa)m(His)n-endo wherein Xaa represents any neutral amino acid residue, and m is integer of 0–4; n is integer of 2–8, and any consecutive two histidines residues can be separated by one or two non-histidine residues; and -endo represents native endostatin sequence.

In another preferred embodiment, said N-terminal additional metal chelating peptide has the following amino acid sequence:

MetGlyGlySerHisHisHisHisHis (SEQ ID NO:1)

In another preferred embodiment, wherein the sequence of the first 15 N-terminal amino acids of the N-terminal modified recombinant endostatin is shown as following:

MetGlyGlySerHisHisHisHisHisSerHisArgAspPhe (SEQ ID NO:2)

In another preferred embodiment, the molecular weight of the endostatin with the additional N-terminal metal chelating peptide sequence is about 21 KDa as determined by reducing gel electrophoresis.

In another preferred embodiment, the endostatin with the additional N-terminal metal chelating peptide sequence is expressed in prokaryote hosts.

In another preferred embodiment, the endostatin with the additional N-terminal metal chelating peptide sequence is isolated in its refolded form.

In a further preferred embodiment, the endostatin with the additional N-terminal metal chelating peptide sequence is able to chelate in vivo or in vitro metal ions and has improved in vivo and in vitro stability.

It is yet another object of the present invention to provide a pharmaceutical composition containing the rhEndostatin protein with any of the N-terminal additional metal chelating peptide sequences as set forth above, wherein said composition comprises human endostatin protein with an N-terminal additional metal chelating sequence as active ingredient, and one or more pharmaceutically acceptable carriers or excipients.

In one preferred embodiment, the rhEndostatin protein with the N-terminal additional metal chelating peptide sequence as described above has the following general formula:

(Xaa)m(His)n-endo wherein Xaa represents any neutral amino acid residue, and m is a integer between 0 and 4; n is a integer between 2 and 8, and any two consecutive histidine residues can be separated by 1 or 2 non-histidine amino acid residues; and -endo represents sequence of native endostatin.

In another preferred embodiment, the additional metal chelating peptide as above mentioned at the N-terminal comprises the following amino acid sequence:
MetGlyGlySerHisHisHisHisHis (SEQ ID NO:1)

In another preferred embodiment, the sequence of the first 15 N-terminal amino acids of the N-terminal modified or elongated recombinant endostatin is shown as following:
MetGlyGlySerHisHisHisHisHisSerHisArgAspPhe (SEQ ID NO:2)

In another preferred embodiment, the molecular weight of the N-terminal modified or elongated rhEndostatin with N-terminal addition metal chelating peptide sequence is about 21 KDa as determined by reducing polyacrylamide gel electrophoresis.

In another preferred embodiment, the endostatin with the additional N-terminal metal chelating peptide sequence is expressed in prokaryote hosts.

In another preferred embodiment, the rhEndostatin with the additional N-terminal metal chelating peptide sequence is isolated in refolded form.

In another embodiment, the rhEndostatin with the additional N-terminal metal chelating peptide sequence is able to chelate in vivo or in vitro metal ions and thereby has improved its in vivo and in vitro stability.

In another preferred embodiment, said pharmaceutical composition further comprises one or more of natural or synthesized or recombinant produced substances having the similar or synergistic effects.

In another preferred embodiment, a method for producing the pharmaceutical compositions as defined is provided, which includes combining a therapeutically effective dosage of endostatin having an additional N-terminal metal chelating peptide sequence, and one or more pharmaceutically acceptable carriers or excipients.

In another preferred embodiment, the pharmaceutical compositions as above set forth are used for production of drugs for treating angiogenesis-related diseases.

In a further preferred embodiment, the pharmaceutical compositions as above are used for the treatment of angiogenesis-related diseases,.

BRIEF DESCRIPTION OF THE DRAWINGS

FIGS. 6A–6B are is RP-HPLC of N-terminal modified rhEndostatin before and after refolding.

FIGS. 12A–12B show the activity of an N-terminal modified rhEndostatin after refolding, assayed with chick embryo chorioallantoic membrane (CAM) method. Left panel (A) is blank control; Right panel (B) shows naked-eye observation of the chick embryo after addition of the refolded, N-terminal modified rhEndostatin.

FIGS. 13A–13B show the inhibitory activity of a refolded, N-terminal modified rhEndostatin on endothelial cell migration in cell migration inhibitory assay using human endothelial cell line (HHEC) established in the lab as target. Left panel (A) is blank control, right panel (B) shows the addition of refolded, N-terminal modified rhEndostatin.

DETAILED DESCRIPTION OF THE INVENTION

Figure 1:
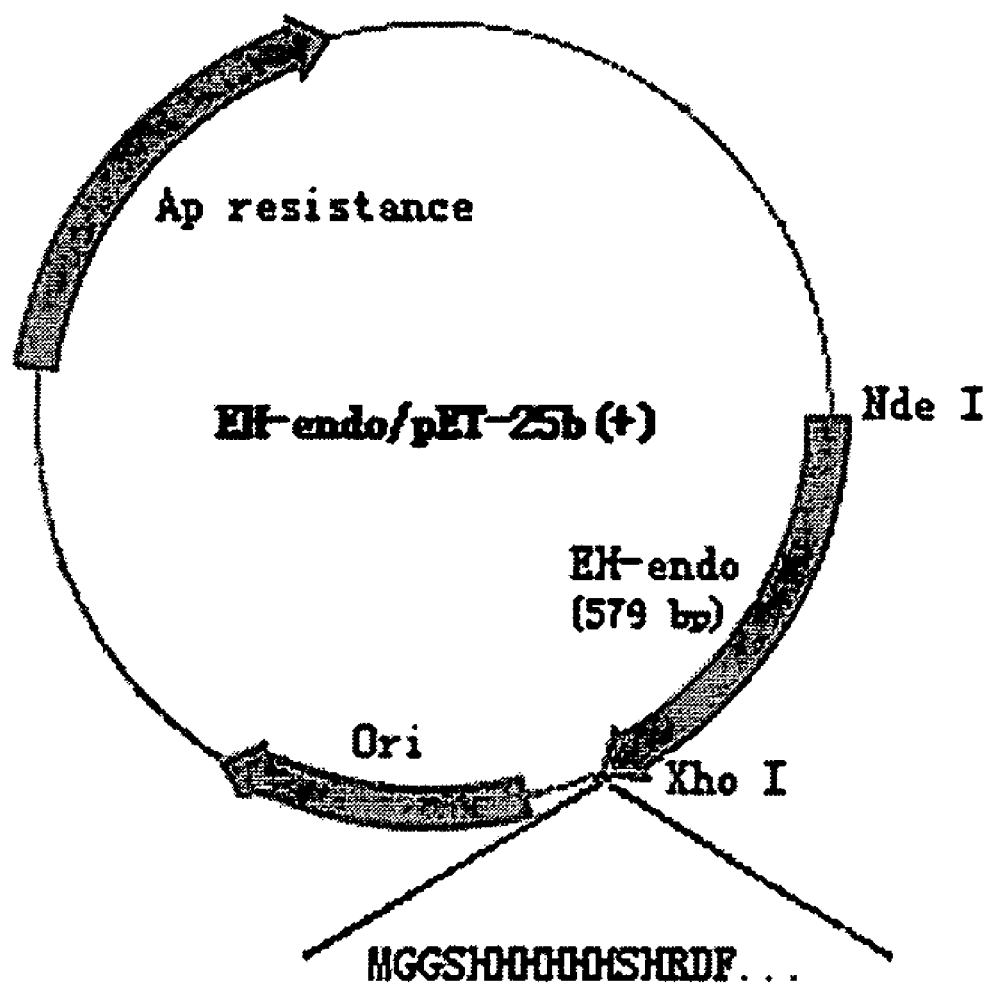
FIG. 1 shows the construction of the recombinant expression plasmid which carries a DNA sequence encoding an N-terminal modified endostatin.

The present invention generally relates to endostatin, especially to recombinant human endostatin (rhendostatin) protein with an N-terminal metal chelating peptide sequence, its preparation, and a method for improving its in vivo stability and activity by modifing recombinant human endostatin. The present invention further relates to recombinant human endostatin with N-terminal modification-including pharmaceutical compositions, and the use of the modified recombinant human endostatin or its pharmaceutical compositions for the treatment of angiogenesis-related disease.

The term "endostatin with N-terminal metal chelating peptide sequence" used herein basically refers to an endostatin molecule comprising at least 2–12 consecutive additional amino acids with metal binding properties at the N-terminal of native endostatin molecule. This term is also sometimes interchangeably referred to as "N-terminal modified rhEndostatin" or "rhEndostatin with additional amino acid sequence at the N-terminal" or "N-terminal elongated rhEndostatin". The so-called addition or modification in this context can be made at the level of DNA or amino acids. In this context, the term sometimes is abbreviated as "EH-endo".

The term "yeast produced native rhEndostatin" used herein usually means Picha system produced, secreted and folded rhendostatin comprising the native 183 amino acids sequence and having a molecular weight of approximately 20 kDa as determined by reducing gel electrophoresis. In the context, this term is sometimes abbreviated as "Y-endo".

Recently, it is routine for the ordinary skilled artisan to produce a desired peptide or protein in a host cell by DNA recombinant technology. For example, genes for desired proteins may be isolated from the genetic material of cells which contain the gene in nature or complementary DNA made from reverse transcribed mRNA or they can be chemically synthesized. The isolated or synthesized gene may be inserted and expressed in host cell systems that produce protein products at high levels. It is necessary then to separate and recover desired proteins from the total amount of protein produced by the host cells. In order to avoid the shortcoming of lack of specificity and protein denaturation caused by environment change, ion-exchange, hydrophobic chromatography, gel filtration and other traditional purification techniques (Porath, I et al., Nature 258: 598–599, 1975) for the first time described solid phase metal ion chromatography for protein fractionation. Porath's teachings include attaching a commonly used iminodiacetic acid (IDA) to a matrix followed by chelating a metal ion to the IDA-containing support resin. Proteins interact with metal ions through one or more of these amino acids (for instance cysteine, histidine) with electron donating side chains. U.S. Pat. No. 4,569,794 described fusion of metal binding peptide to desired recombinant polypeptide through DNA recombinant technology in order to provide a fusion protein that contains both the desired polypeptide and the metal binding peptide. When the fusion protein and other non-target protein contaminants pass the solid phase metal ion column, the fusion protein can bind to the solid phase metal ion through the metal binding peptide, and separate from the contaminants. All these techniques are well known to one of ordinary skill in the art.

During the course of preparing recombinant endostatin by recombinant technology, the present inventors have referenced to O'Reilly et al., (U.S. Pat. No. 5,854,205) previously published technology, engineered in front of the 5' end of the coding region nucleotides that code for additional 2 glycine and 3–6 histidine residues, expressed and purified the desired E. coli-expressed human endostatin with Ni-NTA column. To our surprise, without removal of the fused peptide, our E. coli system expressed human endostatin with 5–9 additional amino acids at the N-terminal which retained original activity and elicited little immunogenic response from the addition of the N-terminal additional amino acids. In particular, our further study discovered that the addition of N-terminal additional sequence improves the stabilities in vivo and in vitro, and the inhibitory activity on endothelial cell migration.

Therefore, according to one object of the present invention, a modified recombinant human endostatin is provided, characterized by having an additional metal chelating peptide sequence at its N-terminal.

In one preferred embodiment, such a human endostatin protein with an N-terminal additional metal chelating peptide sequence as described above has the following general formula:

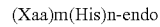
(Xaa)m(His)n-endo wherein Xaa represents any neutral amino acid residue, and m is a integer between 0 and 4; n is a integer between 2 and 8, and any two consecutive histidine residues can be separated by 1 or 2 non-histidine amino acid residues; and -endo represents sequence of native endostatin.

In a particular preferred embodiment, the additional metal binding peptide at the N-terminal contains the following amino acid sequence:

MetGlyGlySerHisHisHisHisHis (SEQ ID NO:1)

In a further particular preferred embodiment, the sequence of the first 15 N-terminal amino acids of the N-terminal modified recombinant human endostatin is shown as the following:

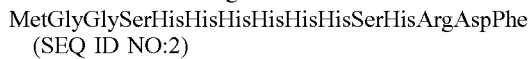
MetGlyGlySerHisHisHisHisHisHisSerHisArgAspPhe (SEQ ID NO:2)

In the sequence as set forth in SEQ ID NO: 1, Met is a specific N-terminal starting amino acid for E. coli expressed recombinant protein. In some special cases, E. coli may cleave Met and produce a mixture of recombinant protein with and without the starting Met. Thus, the N-terminal may have or may not have such a Met residue, and the protein would still be within the scope of the subject invention. GlyGlySer following the Met residue is designed to increase endosatin expression efficiency. These amino acids may be either one, or several consecutive residues. Additional sequence HisHisHisHisHis (amino acids 5 through 9 of SEQ ID NO:1) is designed based on the property that histidine can chelate metal ions such as $Ni^{2+}$, $Zn^{2+}$, and $Cu^{2+}$ (as mentioned before). Several consecutive histidines can increase the binding chance and ability to chelate metal ions. Nevertheless, there can be one or several other amino acids between individual histidines or between peptides composed of 2 or more N-terminal histidines, and the non-histidine amino acid insertion does not affect the metal binding property of the additional sequence. Because in this case, though there is spacing residue in the primary sequence of the additional sequence, peptide folding can make multiple histidines form a close spatial structure and increase the chelating chance and ability between the molecule and metal ions.

By using DNA manipulation techniques including preparation and modification of gene sequences, construction of recombinant vectors and expression of the desired biologically active polypeptides, and separation and purification of the expressed products and the like (see, for instance, Sambrook et al, Molecular Cloning: A Laboratory Manual, 2nd. Ed., Cold Spring Harbour Press, 1989, which incorporated herein by reference), the persons of ordinary skill in the art can readily prepare recombinant human endostatin with the additional N-terminal metal chelating peptide sequence according to the present invention. For example, using polymerase chain reaction technique (PCR), it is possible to extract from human tissue cDNA library DNA fragments coding for human endostatin and amplify it in a cloning vector and modify it accordingly. For the convenience, it is possible to design appropriate oligonucleotides (including forward and reverse) based on the sequence of designed additional amino acids sequence and the native N-terminal sequence of endostatin, and in the presence of DNA polymerase and four kinds of deoxynucleotides, to synthesize the desired nucleotide sequence by PCR technique. For example, it is possible to design a primer with sequence that at the 5'-end contains nucleotides coding for the N-terminal additional amino acids and also has joined one or more restriction enzyme sites for later splicing and ligating into a suitable vector.

For example, in order to obtain the human endostatin gene having a 5' nucleotide sequence coding for the additional amino acids (SEQ ID NO:1), it is possible, based on a desired N-terminal amino acid sequence and known full length sequence of endostatin, to use DNA synthesizer to synthesize a pair of primers that contain DNA sequences coding for the additional amino acids and appropriate restriction sites. Then it is possible to perform PCR reaction in the presence of 4 kinds of nucleotides and Taq DNA polymerase with complementary DNA (cDNA) isolated from human liver tissues as template. Because a corresponding nucleotide sequence that encodes the N-terminal additional amino acid sequence has been incorporated into the synthesized oligonucleotide, after PCR amplification the full length endostatin (579 bps) with nucleotide sequence at the 5'-end that encodes the additional amino acid sequence and appropriate restriction sites is obtained.

Then the obtained gene fragment is ligated into an appropriate cloning vector and expressed in, for example, *E. coli* host cells. These transformed cells can be incubated on appropriate media and after selection of positive clones, DNA can be isolated from the cells for restriction analysis to confirm the accuracy of the fragment or, alternatively, confirm by full length nucleotide sequencing analysis in two orientations.

After that, the rhEndostatin-encoding fragment having a sequence coding for the additional N-terminal amino acid sequence and with DNA pieces containing appropriate restriction sites at two ends is ligated to appropriate expression vector, for instance pET25B containing T7 promoter and have been linealized by same restriction enzymes and signal peptide sequence removed. By means of methods known to the ordinary skilled artisans, the resultant recombinant expression construct is transformed into a host that is suitable for the expression of the desired endostatin protein, for instance, *E. coli* BL21(DE3) system. The transformed *E.coli* cells are incubated under suitable conditions and the protein expression results. The amino acid sequence of the desired expression product is (Met)GlyGlyXaaHisHisHisHisHis-endostatin (wherein Xaa has the same meaning as above) (SEQ ID NO. 11), and as a specific example (Met)GlyGlySerHisHisHisHisHis-endostatin (with reference to example 1) (SEQ ID NO: 1).

Based on known amino acid sequences, skilled artisans can also take advantage of known peptide synthesis techniques to prepare rhEndostatin or its functional equivalents having an additional N-terminal metal chelating peptide sequence.

Our experimental results show that the modified rhEndostatin of the present invention produced in prokaryotes, for example, *E. coli*, not only can be isolated in refolded form, but also show markedly improved storage and in vivo stability, thereby markedly improving its biological activity, compared to yeast-produced native endostatin.

Thus, according to the present invention, a method for modifing rhEndostatin to improve its in vivo stability and biological activity is disclosed. The method includes modifying the DNA coding sequence for rhEndostatin protein, so that the resulting expressed endostatin protein has an additional metal chelating peptide sequence at its N-terminal.

In a preferred embodiment, the rhEndostatin protein with an additional N-terminal metal binding peptide sequence as disclosed has the following formula:

(Xaa)m(His)n-endo wherein Xaa represents any neutral amino acid residue, and m represents any integer between 0–4; n is any integer between 2 and 8 and any 2 consecutive histidine residues could be separated by 1 or 2 non-histidine amino acid residues; and -endo represents native endostatin sequence.

In a more preferred embodiment, the N-terminal metal binding peptide as disclosed has the following shown amino acid sequence:

MetGlyGlySerHisHIsHisHisHis (SEQ ID NO:1)

In a particularly preferred embodiment of the present invention, the sequence of the first 15 N-terminal amino acids of the N-terminal modified recombinant endostatin is shown as following:

MetGlyGlySerHisHisHisHisHisSerHisArgAspPhe (SEQ ID No:2)

In a more particularly preferred embodiment, the N-terminal modified rhEndostatin has a molecular weight of approximately 21 KDa as determined by reducing polyacrylamide gel electrophoresis.

In another preferred embodiment, the modified recombinant endostatin protein with N-terminal additional metal chelating peptide is expressed in prokaryotes.

In still another preferred embodiment, the modified rhEndostatin with a N-terminal additional metal chelating peptide is isolated in refolded form.

In a further preferred embodiment, the modified rhEndostatin with a N-terminal additional metal chelating peptide can chelate metal ions in the in vivo or in vitro environment, and has improved in vitro and in vivo stability compared to its parent human endostatin.

One of ordinary skill in the art can recover and purify the expressed protein from the transformed *E. coli* host. For example, these methods include, but are not limited to, ammonium sulfate precipitation, ion-exchange chromatography, hydrophobic chromatography, gel filtration and affinity chromatography, particularly above mentioned Ni-NTA affinity chromatography, or a combination thereof. For the purpose of this invention, although it is preferred to use Ni-NTA affinity chromatography to recover and purify the endostatin with the additional N-terminal sequence, it is still possible to obtain with high yield and high purity the desired protein by a combination of cation and anion exchange chromatography (with reference to example 2).

It is worthy of mention that the practice of purifying the desired protein under denaturation conditions and then performing large-scale refolding will markedly increase the recovery of the refolded protein. On the other hand, refolding also benefits further purification of the desired protein.

After purification, the EH-endo made by known methods as above described is subjected to quantitative protein analysis. The results show that the production yield for the desired protein after refolding as obtained by the method mentioned above is about 500 mg/L fermentation broth. This yield is markedly higher than the productivity as published for E. coli or yeast system produced recombinant endostatin. This improvement of production yield is not only due to the incorporation of the sequence encoding the N-terminal additional amino acids, but also resulted from the high recovery of the final product.

Various methods can be used to finish protein refolding, for example, it is possible to use glutathione in reduced and oxidized states and different concentration of urea in Tris buffer (refolding buffer) to treat protein. Though O'Reilly et al. (for instance O'Reilly, M. S. et al., Cell 88: 277–285, 1997) reported that unfolded insoluble endostatin demonstrates the same inhibition activity on capillary endothelial cell proliferation in vitro and cancer growth in vivo, our research showed that the maximal degree of full renaturation under refolding condition is important to reduce protein toxicity, and to improve the biological activity and stability of E. coli produced proteins (see also example 6 and 7).

A series of experiments demonstrate that rhEndostatin with N-terminal additional sequence according to the present invention indeed mostly get refolded after the separation, purification and refolding treatment. Methods for determination of protein refolding include: reverse phase high pressure liquid chromatography (RP-HPLC), Sodium dodecyl sulfate-polyacrylamide gel oxidative-reductive electrophoresis (oxidative-reductive SDS-PAGE), enzyme linked immunoassay (ELISA), cys-cys bond analysis, circular dichroism (CD) analysis, fluorescence spectrum analysis, chick embryo chorioallantoic membrane (CAM) assay, and cell migration inhibition assay (reference to example 4).

It is possible to use thrombin to remove the N-terminal additional sequence of the rhEndostatin, for example, thrombin can be added at 1:200 ratio to the purified protein solution and incubated at 23° C. for 30 minutes. Then gel filtration chromatography can be used to separate the hydrolyzed fragments. However, the present inventors found that without removal of the N-terminal additional His and its directly adjoining GlyGlySer sequence did not only lead to the improvement of in vitro stability of the final products, but also did not cause any immunological reactions (data not shown).

Figure 8:
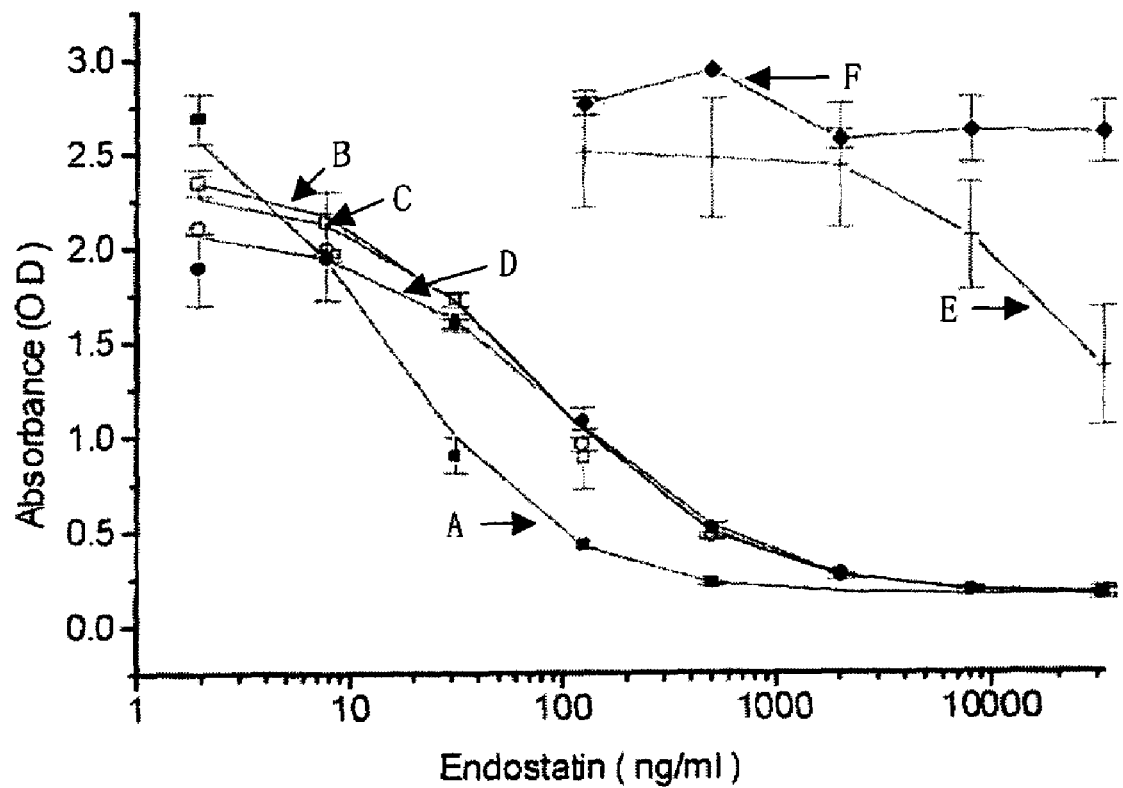
FIG. 8 shows different antibody-antigen recognition reactions for an N-terminal modified recombinant endostatin before and after refolding during ELISA assay. A is the sample standard from the detection kit; B, C, and D are samples from different batches of refolding; E is sample before refolding; F is the supernatant of fermentation broth.

According to well-known methods, EH-endo purified from ion exchange column was analyzed by SDS-PAGE using 12% polyacrylamide. Results showed that EH-endo exhibits an apparent molecular weight of around 21 KDa under reducing condition (for example, treated with elution buffer containing 1 M beta-mercaptoethanol) (FIG. 1). To determine the immunological reactivity of the EH-endo prepared as above, an Enzyme Linked Imunoassay (ELISA) analysis using a pre-prepared EH-endo antibody can be carried out (FIG. 8).

Because oligonucleotide sequences encoding (Xaa)m (His)n (wherein Xaa, m and n all have the same meaning as defined above), and specifically encoding the additional metal binding peptide sequence GlyGlySerHisHisHisHisHis (amino acids 2 through 9 of SEQ ID NO: 1), have been incorporated into the 5' end of the known native endostatin gene sequence, the resulting N-terminal of the endostatin with additional amino acid according to the present invention brings about the following two positive consequences when compared to current available technology. First, after the incorporation of the nucleotide encoding GlyGlySer, the starting efficiency of DNA transcription and transcript translation is markedly increased, and this provides necessary conditions for the improvement of productivity. Our previous experimental results showed that if the encoding sequence for (Met)GlyGlySer is deleted, the expression efficiency of endostatin protein is only about 1% of total bacterial protein; In contrast, the addition of N-terminal (Met)GlyGlySer sequence increases the production yield of endostatin protein to about 30% of total cellular protein. In addition, incorporation of GlyGlySer helps to protect the protein from the hydrolysis of proteinases. Second, the incorporation of (His)2-5 immediately after GlyGlySer is mainly for the binding of the histidines to metal ions to improve the stability and biological activities of the final product (details follow).

While not intended to be bound by theory, it is believed that these may be attributed to the fact that the addition of multiple histidine residues at the N-terminal possibly increases the binding chance and ability of human endostatin to metal ions, including zinc, in its surroundings.

Two different kinds of results were obtained from the relevant published research. On the one hand, Boehm et al. (Boehm, T. et al., Biochem. Biophys. Res. Commun., 252: 190–194, 1998) show that there is a $Zn^{2+}$ binding site at the N-terminal of Endostatin molecule and this binding is necessary for endostatin's inhibitory activity on blood vessel formation. Also, Earlier crystal analysis research by Ding et al. (Yuan-Hua Ding et al., Proc. Natl. Acad. Sci. USA, 95: 10443–10448, 1998) found that zinc is a constituent of endostatin and indicates that $Zn^{2+}$ possibly affects molecular activation or expression of its activity on blood vessel formation either indirectly by stabilizing the tertiary structure or more directly if the N-terminal loop structured around the zinc is involved in activity, such as through endostatin dimer formation. In contrast, Noriko Yamaguchi et al., (The EMBO J., 18:4414–4423, 1999)found in experiments using cultured cell and metastatic tumors bearing mice models that Zn-free endostatin inhibits VEGF-induced HUVEC cell migration to the same extent as wild type endostatin, and that Zn-free endostain causes regression of renal carcinoma in vivo as effectively as Zn-containing endostatin. The authors believe that the conclusion of Boehm et al. is due to the use of unfolded endostatin and the decreased activity observed by Boehm et al. (1998) could have been a refolding artifact and not an effect directly due to the Zn binding. In addition, Kim et al. (B. Kim Lee Sim et al., Angiogenesis, 3: 41–51, 1999) showed later that elimination of the necessary $Zn^{2+}$ binding site His1 and His3 of endostatin does not change the endogenous cancer inhibitory activity of recombinant human endostatin. That is, the truncated form of rhEndostatin missing 4 N-terminal residues inclusive of His1 and His3 as well as the intact rhEndostatin were both found to inhibit the growth of primary tumors and metastases.

In the face of these two contradictory conclusions, the subject invention is significant. First, our in vitro experiments show that the existence of metal ion $Zn^{2+}$ is very important for endostatin to maintain its in vitro biological activity. For example, after EDTA treatment and repeated dialysis to remove all metal ions, the solutions of endostatin from various sources were added with zinc and the resulting mixtures were stored at different temperatures for sufficiently long time. The results showed that even though storing the samples at relatively high temperature (37° C.) for 15 days in the presence of $Zn^{2+}$, the rhEnodstatin with the additional N-terminal metal chelating peptide according to the present invention still behaves as monomers. On the contrary, increase of protein oligomers and accompanying decrease of protein stability was observed in the presence of $Zn^{2+}$ for the yeast-expressed native endostatin that had been stored for equal length of time. Similarly, in the absence of $Zn^{2+}$ even if stored for a relatively short time, the E. coli-produced endostatin protein with additional N-terminal sequence displayed a decreased stability (example 5). In addition, after heat treatment for different length of time, the specific antibody binding activities of the rhEndostatin with additional N-terminal metal chelating peptide as described herein and yeast-produced native endostatin that contains no additional sequence were determined at room temperature by specific competitive assay using a commercially available ACCUCYTE endostatin immunological detection kit (ACCUCYTE Human Endostatin™). The results showed that rhEndostatin with additional N-terminal metal chelating peptide of this invention has obviously better antibody binding activity and heat tolerance ability than yeast system expressed native rhEndostatin (example 6).

Furthermore, pharmacokinetics and pharmacological activity studies were performed in animals using the rhEndostatin with N-terminal metal chelating peptide of the present invention and native rhEndosatin produced by yeast system, respectively. Those results showed that rhEndostatin with N-terminal metal chelating peptide according to the present invention has increased half-life and markedly reduced clearance rate, and also demonstrated that the rhEndostatin with N-terminal metal chelating peptide has a better in vivo stability than yeast system produced native rhEndostatin (see example 5). Corresponding results were also reproduced in inhibition experiments of tumor growth using a mouse xenograft model, for example, to reach similarly growth-inhibitiory level, the administration dosage of the rhEndostatin with N-terminal metal chelating peptide is only about 1/10 of that of the yeast produced native human endostatin (see example 8). This is attributed to the improved protein stability, which results in improved in vivo maintenance time for the biological activity (see example 5).

Thus, the rhEndostatin with N-terminal metal chelating peptide of this invention has markedly improved in vitro physical and chemical stability compared to native rhEndostatin expressed in *Pichia* yeast. It is understandable to the ordinary person skilled in the art that a preferred embodiment of the modified endostatin according to the present invention has 5 more metal binding positions at the N-terminal, resulting in increased metal, particularly $Zn^{2+}$, binding chance and ability relative to the native species.

It is still another object of the present invention, to provide a pharmaceutical compositions useful for treatment of angiogenesis-related diseases, comprising as an active ingredient a therapeutically effective amount of rhEndostatin protein with the additional N-terminal metal chelating sequence, and one or more pharmaceutically acceptable carriers or excipients.

According to this object of the present invention, the rhEndostatin protein with the N-terminal additional metal chelating peptide sequence has the following general formula:

(Xaa)m(His)n-endo wherein Xaa represents any neutral amino acid residue, and m is a integer between 0 and 4; n is a integer between 2 and 8, and any two consecutive histidine residues can be separated by 1 or 2 non-histidine amino acid residues; and -endo represents sequence of native endostatin.

In one preferred embodiment, the additional metal chelating peptide at the N-terminal has the following amino acid sequence:

MetGlyGlySerHisHisHisHisHis (SEQ ID NO:1)

In another preferred embodiment of the present invention, the sequence of the first 15 N-terminal amino acids of the N-terminal modified recombinant endostatin is shown as following:

MetGlyGlySerHisHisHisHisHisHisSerHisArgAspPhe (SEQ ID No:2)

In a particularly preferred embodiment, wherein the N-terminal modified recombinant endostatin has a molecular weight of approximately 21 KDa as determined by reducing polyacrylamide gel electrophoresis.

In another preferred embodiment, the modified rhEndostatin protein with N-terminal additional metal chelating peptide is expressed in prokaryotes.

In yet another preferred embodiment, the described recombinant endostatin with N-terminal additional metal chelating peptide is isolated in refolded form.

In still yet another preferred embodiment, the rhEndostatin with N-terminal additional metal chelating peptide can chelate metal ion in the in vivo or in vitro environment and has an improved in vitro and in vivo stability compared to its parent endostatin.

In general with respect to the pharmaceutical compositions as defined above, the active ingredient also includes one or multiple natural or synthesized or recombinant produced materials having similar or synergistic effect. These materials include, but are not limited to, for example, other anticancer agents and other angiogenesis inhibitors selected from the group consisting of angiostatin, restin, canstatin and tumstatin, and immunological modulators such as interleukin, interferon, thymulin, and tumor necrosis factor and other immunomodulators.

The present invention further provides a method for formulating a pharmaceutical composition comprising mixing a therapeutically effective amount of modified rhEndostatin protein with the N-terminal metal chelating peptide sequence as described herein as an active ingredient together with one or more pharmaceutically acceptable carriers or diluants at suitable ratio, by well known processes (see, for example, Remington's Pharmaceutical Science. 15th ed., Mack Publishing Company, 1980).

Based on different administrating routes, the pharmaceutical compositions according to the present invention can be formulated to various formulations suitable for parenteral administration including intravenous, intramuscular, intracaveties (for instance, intra-thoracic, intra-peritoneal, intracranial, intracerebral, intravaginal, intraspinal, or intracerebroventricular etc.) using suitable carriers and excipients.

The pharmaceutical forms suitable for injection or infusion use can include sterile aqueous solutions or dispersions, or sterile powders comprising the active ingredients that are adopted for the extemporaneous preparation of sterile injectable or infusible solutions or dispersions.

The carriers that are suitable for preparing parenteral administration formulations can be solvents or dispersing medium containing, for example, sterile distilled water, water for injection, saline or glucose solution, or low concentration (such as 1–100 mM) phosphate buffer (PBS), and solvent or dispersing medium that contains ethanol, polyglycol (for instance glycerol, ethylene glycol, propylene glycol and liquid polyethylene glycol, and the like). In all circumstances, preparations or formulations that are sterile, flowable, and stable under the conditions of manufacture and storage, and suitable for administrating by syringe, are preferred. Proper fluidity can be maintained, for example, by the use of a coating such as lecithin, by the maintenance of the required particular size in the case of dispersion, and by use of surfactants. Additionally, various additives which enhance the stability, sterility, and isotonicity of the compositions, including antimicrobial preservatives, antioxidants, chelating agents, and buffers, can be added. In many cases, it will be desirable to include isotonic agents, for example, sugars, sodium chloride, and the like.

In summary, sterile injectable solution can be prepared by incorporating the active proteins utilized in practicing the present invention in a desired amount and in an appropriate solvent with various other ingredients enumerated above, as required, followed by filter sterilization. In the case of sterile powders for the preparation of sterile injectable solutions, the preferred methods of preparation are vacuum drying and lyophilizing techniques, which yield a powder of the active ingredient plus all additional desired ingredients present in the previously sterile-filtered solutions.

A pharmacological formulation described and claimed herein can be administered to the human patient in an injectable formulation containing any compatible carrier, such as various vehicles, adjuvants, additives, and diluents; or the compounds utilized in the present invention can be administered parenterally to the patients in the form of sustained-release subcutaneous implants or targeted delivery systems, such as polymer matrices, liposomes, and microspheres. An implant or other biocompatible delivery modules are designed such that the active ingredients are slowly released over a period of several days to several weeks.

Depending upon the practical requirements, besides the rhEndostatin protein with the N-terminal metal binding peptide as an essentially active ingredient, pharmaceutical compositions of the present invention can also contain one or more other natural or synthesized active ingredients or its mixture that share a common or similar biological activity and produce supportive or synergistic effect, but not antagonize to each other.

The other active ingredients used in a pharmaceutical composition in accordance with this invention can include, but are not limited to, natural anticancer agents (for instance nitrogen mustara, cyclophosphamide, vincristine, paclitaxel, daunomycin, and the like), other angiogenesis inhibitor (for instance recombinant angiostatin, restin, canstatin, and tumstatin ), and immunological modulators (interleukin, interferon, thymulin, and tumor necrosis factor, etc.) and the like.

Another embodiment of the present invention relates to the use of the rhEndostatin protein with the N-terminal metal binding peptide sequence or its pharmaceutical compositions in treating or reducing angiogenesis-related diseases or in preparing medicaments for the treatment of these diseases. Angiogenesis-related diseases include but are not limited to angiogenesis-dependent cancer, diabetes retinopathy, and arthritis, etc.

Therefore, the present invention is further related to methods for treatment of angiogenesis-related diseases, especially for angiogenesis-dependent cancers, comprising administering to a human patient an N-terminal modified or elongated rhendostatin according to the present invention, which inhibits and reduces growing tumors by inhibiting capillary endothelial migration and proliferation, wherein the N-terminal modified or elongated rhEndostatin has the following general formula:

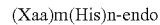

(Xaa)m(His)n-endo wherein Xaa represents any neutral amino acid residue, and m is a integer between 0 and 4; n is a integer between 2 and 8, and any two consecutive histidine residues can be separated by 1 or 2 non-histidine amino acid residues; and -endo represents sequence of native endostatin.

In one preferred embodiment, the additional metal chelating peptide at the N-terminal has the following amino acid sequence:

MetGlyGlySerHisHisHisHisHis (SEQ ID NO:1)

In another preferred embodiment of the present invention, the sequence of the first 15 N-terminal amino acids of the N-terminal modified recombinant endostatin is shown as following:

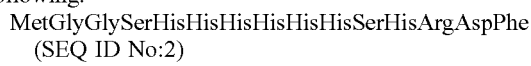

MetGlyGlySerHisHisHisHisHisSerHisArgAspPhe (SEQ ID No:2)

In a particularly preferred embodiment, wherein the N-terminal modified or elongated rhEndostatin has a molecular weight of approximately 21 KDa as determined by reducing polyacrylamide gel electrophoresis.

In another preferred embodiment, the N-terminal modified or elongated recombinant human endostatin protein with N-terminal additional metal chelating peptide is expressed in prokaryotes.

In yet another preferred embodiment, the N-terminal modified or elongated rhEndostatin is isolated in refolded form.

In still yet another preferred embodiment, the N-terminal modified or elongated rhEndostatin can chelate metal ions in in vivo or in vitro surroundings and has an improved in vitro and in vivo stability compared to the parent endostatin.

According to the present invention, the N-terminal elongated endostatin may be used in combination with other compositions and therapies for angiogenesis-related diseases. A tumor, for example, may be treated conventionally with surgery, radiation, or chemotherapeutics combined with elongated rhEndostatin of the present invention, and then the modified endostatin can be administered to the patient to stabilize any residual primary tumor.

Overall efficacy of a drug to a great degree depends, in principle, on administering dosage and pathway. The choice of administering dosage and pathway is thus very important. In general, the choice is made based upon pharmacokinetics (for example, biological half-life, absorbance characteristics, receptor binding and clearance) and pharmacological property (for example biological activity, concentration-effect relationship of the drug). Though increase of drug concentration under some circumstances is correlated with increase of drug effect, the stability of drug (including in vitro storage stability and in vivo half-life) is also a pharmacological parameter that needs to be taken into consideration for the determination of concentration-pharmacological effect relationship. Thus for endostatin, improvement of its in vivo stability is important for the reduction of administrating-dosage and long-term maintenance of relatively low but effective concentration of the drug.

Generally, the therapeutically effective amount of compositions of this invention ranges from about 0.01 to 100 mg/kg/day, preferably about 1 to 80 mg/kg/day, more preferably about 5 to 50 mg/kg/day. In general, a therapeutic amount between 0.05 to 100 mg/kg/day, preferably between 0.1 to 80 mg/kg/day, and more preferably between 0.5–50 mg/kg/day is especially effective for intraperitoneal or intramuscular administering, while 0.01 to 100 mg/kg/day, preferably 0.05 to 80 mg/kg/day, more preferably 0.1 to 50 mg/kg/day if administered intravenously. The skilled artisan will appreciate the optimum dosage required to effectively treat a subject and it should be individually determined depending upon various factors including the dosage form employed and the route of administration utilized, the severity of the disease to be treated, previous treatments, the general health, age and weight of the subject, and the sensitivity, tolerance of patients toward the treatments by clinicians, all as is well known and routine to those of ordinary skill in the art. Worth particular mention here is that it is hard to determine a universal optimal biological dosage and maximal tolerance dosage because there is no obvious toxicity for endostatin and the difference of sensitivity for different cancer tissues is greatly variable.

Though based on what is just described, industrial scale and low cost production of high yield, and high purity recombinant human endostatin is possible, all this has to be based on the assumption that the obtained product has biological activity that is sufficiently high and suitable for clinical application. Various methods used for the detection of the biological activity of endostatin protein have been established, and these methods include in vitro endothelial cell proliferation and/or migration assay; mice corneal angiogenesis assay (Kenyon, B. M. et al., Invest. Ophthalmol. Vis. Sci. 37:1625–1632, 1996); Chick embryo chorioallantoic membrane (CAM) assay; rabbit corneal pocket assay and the inhibition assay of modified endostatin on the in vivo growth and/or metastasis of implanted tumors ( for example, murine melanoma B16-BL6, hepatocellular carcinoma H22, LLC-LM primary tumor, Lewis lung carcinoma, fibroblastoma T241, melanoma B16F10, renal cell carcinoma 786-0, and human hepatoma SMMC-7721).

Though many standard endothelial system and cancer animal models for the detection of endostatin biological activity lack sufficient sensitivity and specificity, our experimental results with endothelial cell system established in the lab shows that EH-endo as described above has better inhibitory activities for the endothelial cell migration (in vitro) and cancer growth in the tumor-bearing mice (in vivo) than the native endostatin without N-terminal additional amino acid sequence (for instance Y-endo).

Compared to native recombinant human endostatin produced by yeast expression system, *E. coli* expressed recombinant human endostatin with additional amino acids at the N-terminal not only refolded in vitro, but also showed markedly improved in vivo and in vitro stability, and increased inhibitory activity on endothelial cell migration.

Further details of the present invention will be apparent from the following Examples and the accompanying drawings which are included by way of illustration, not by way of limitation, of this invention. This application is intended to cover those changes and substitutions which may be made by those skilled in the art without departing from the spirit and the scope of the appended claims.

All publications, patents, and patent applications cited herein are hereby incorporated by reference in their entirety, to the extent they are not inconsistent with the explicit teachings herein.

EXAMPLES

Example 1

Construction of the N-terminal Modified rhEndostatin

Based on known amino acid sequence of endostatin protein and intended additional N-terminal sequence, PCR primers were designed and synthesed to amplify endostatin-coding DNA sequence from human liver cDNA library (Invitrogen) using Pfu DNA polymerase (Stratagene). The forward primer includes the following additional sequence CATATGGGGGGTTCTCATCACCATCACCATCAC (SEQ ID NO:3), introducing an NdeI site and another 27 nucleotides that together code for 10 additional amino acids in front of native endostatin. The reverse primer CTCGAGCTACTTGGAGGCAGTCATGAAGC (SEQ ID NO:4), which can anneal to the sequence at the end of endostatin, has an introduced XhoI site. PCR reaction was performed as 94° C., 1' for denaturation, 60° C., 1' for annealing and 72° C., 1'30" for extension, and for 30 cycles all together.

After amplification, QIAquick PCR product purification kit (Qiagen) was used to purify the amplified product. Thereafter, Purified product was cloned into PCRscript (Stratagene). After sequence confirmation, the insert was excised with restriction enzymes NdeI and XhoI and cloned into the NdeI/XhoI site of the vector pET25B (Novagen) to obtain EH-ENDO/pET25B (FIG. 1). The final construct was introduced into competent BL21 (DE3) *E. coli* cells to express the protein. The accuracy of the final product was confirmed by restriction enzyme digestion with NdeI/XhoI, HindIII/SacII, and NdeI/SmaI, resulting in fragments sizes 0.6 Kb and 5.4 Kb, 0.28 Kb and 5.7 Kb, 0.32 Kb and 5.7 Kb, respectively and by re-sequencing the insert.

Example 2

Expression and Purification of the Modified rhEndostatin with the Additional N-terminal Sequence EH-ENDO/pET25B transformed BL21(DE3) clone was inoculated in a flask with LB medium and grown in 37□ shaker. After enough bacteria was obtained, this bacteria was seeded into 20 liter fermentor for further incubation. When $OD_{600}$ reached about 10, the bacteria was again transferred to 300 liter fermentor and grew until OD reached about 30. 1 mM isopropyl-beta-D-thiogalactoside (IPTG) was added to induce expression of the protein. After 3–4 hours, the bacterial cells were pelleted and resuspended in a buffer supplemented with 8 M urea, 10 mM Tris-HCl (pH 8) and 100 mM sodium phosphate and incubated for an hour at room temperature.

Mechanical method was used to disrupt the bacterial cells. Inclusion body was obtained with centrifugation (20,000 g, 20 minutes) and was washed with deoxycholic acid that contains 2% Triton X-100. Inclusion body was dissolved in Tris-HCl (PH8) buffer supplemented with 8 M urea and 50 mM beta-mercaptoethanol and incubated for another 1 hour.

Then after 10,000 g centrifugation for 25', the inclusion body of the dissolved recombinant protein was pelleted. BPG300/500 chromatography columns (Pharmacia), with anion and then cation exchange chromatography, were used to purify the desired protein. The used anion and cation resin are Q-FF (Pharmacia) and SP-FF (Pharmacia) respectively. After these two steps of chromatography purification, protein purity reached above 90%.

After desalting the elution product, refolding was performed on the purified modified ndostatin. For example, the EH-endo protein prepared as above was diluted into 10 mM Tris-HCl buffer (pH8.0) at a protein concentration of 0.5 mg/ml, and then a solution containing 8M urea, 20 mM beta-mercaptoethanol, 5 µM ZnSO4 and 10 µM CuSO4 was added thereto. After that, the solution was added at a rate of 1 ml/min onto Ni-NTA column pre-equilibrated with 10 mM Tris-HCl. After loading, 10 mM Tris-HCl buffer (pH 8.0) containing 5 µM ZnSO4 and 10 µM CuSO4 (refolding buffer) was used at a flow rate of 1 ml/min for refolding treatment (about 10 hours). Then elution solution (10 mM Tris-HCl buffer containing 500 mM imidazole, pH 8.0) was used to elute the Ni-NTA bound protein. After this refolding treatment, insoluble endostatin becomes soluble. This refolding also serves as another step for protein purification. The level of protein refolding can be determined by the alteration of their physical and chemical properties under SDS-PAGE, HPLC, CD, fluorescence spectroscopy, disulphide bonding test, etc.

Figure 2:
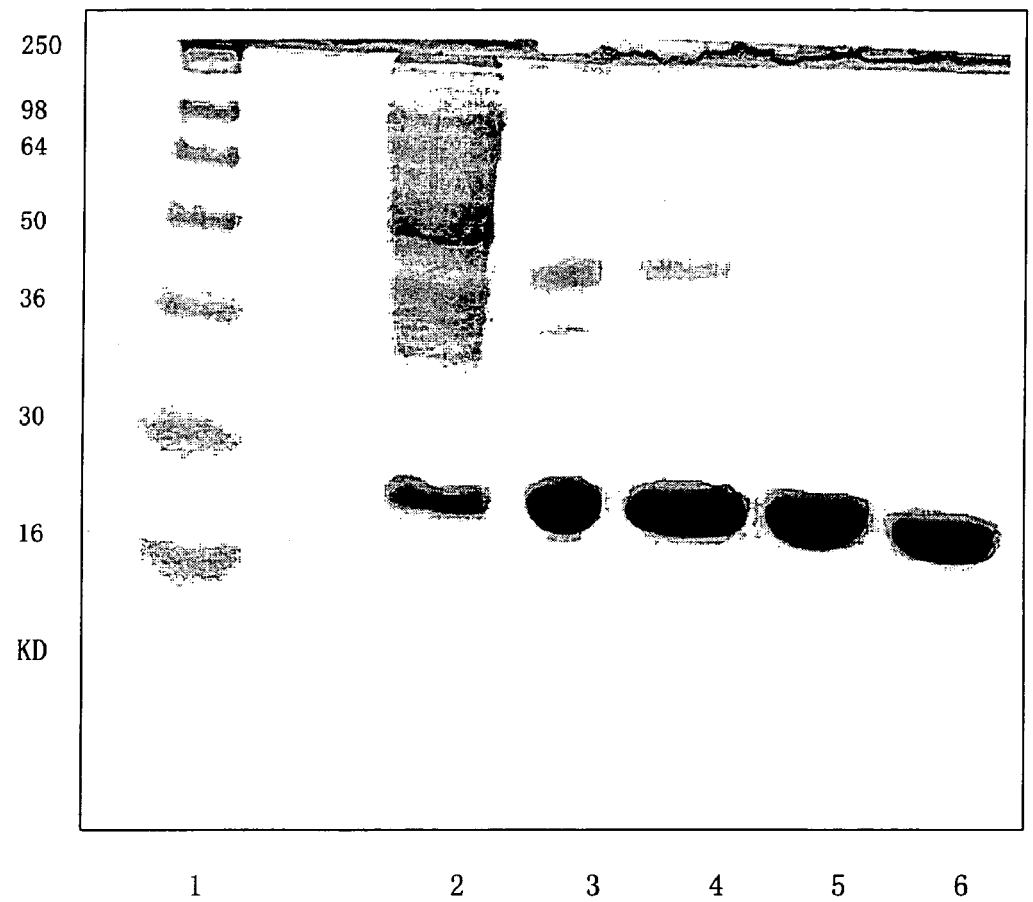
FIG. 2 shows the SDS-PAGE analysis of the rhEndostatin during its purification. Wherein Lane 1: molecular weight marker; Lane 2: solublized inclusion body; Lane 3: rhEndostatin after SP-FF chromatography purification under denatured condition; Lane 4: rhEndostatin after Q-FF chromatography purification under denatured condition; Lane 5: rhEndostatin after refolding, under reducing condition; Lane 6: rhEndostatin after refolding, under oxidizing condition.
Figure 3:
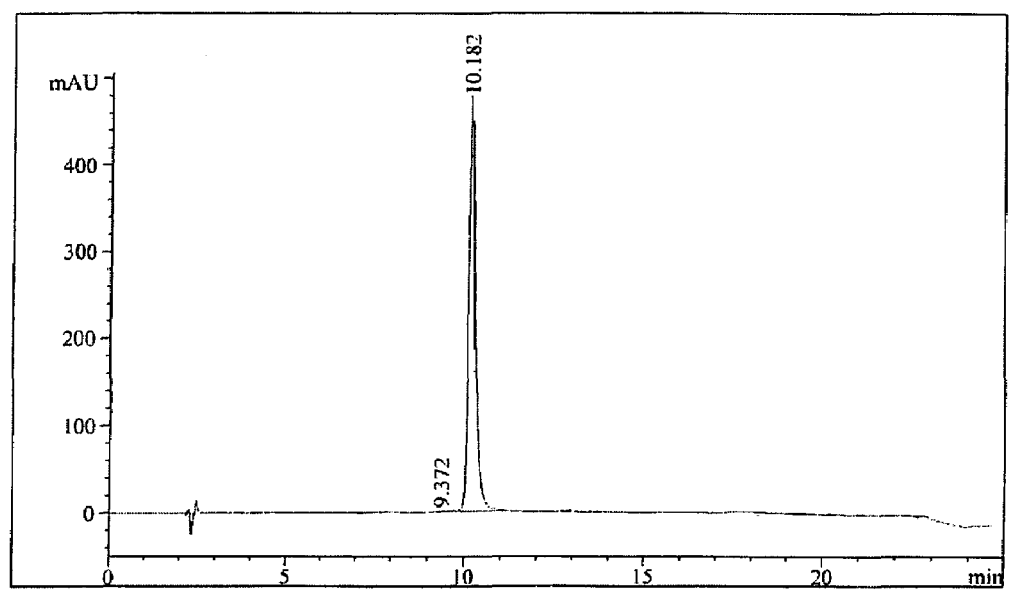
FIG. 3 shows HPLC analysis for an N-terminal modified rhEndostatin during purification.

After dialyzed against 50 M HAc-NaAc buffer, the refolded protein was analyzed with SDS-PAGE and HPLC for purity determination (FIGS. 2 and 3). SDS-PAGE revealed a discrete band of approximately 21 kDa purified to apparent homogeneity for the *E. coli*-derived recombinant protein. Quantitative analysis of the modified endostatin (EH-endo) showed productive yield of about 500 mg refolded protein/liter fermentation broth.

Thrombin dissolved in 20 mM Tris-HCl buffer supplemented with 100 mM NaCl might be added to remove the additional N-terminal amino acid sequences by incubating at 24° C. for about 20 minutes. After hydrolysis, gel filtration resin Superdex 75 HR 10/30 (Pharmacia) can be used to remove the hydrolyzed peptide, or the refolded protein can be directly used in the following physical and biological activity analysis without the hydrolysis treatment.

Example 3

Construction of Native rhEndostatin in Yeast Expression System, Its Expression and Purification Briefly, the sequence encoding human endostatin was amplified by PCR using Taq DNA polymerase (Stratagene), forward PCR primer (5'-CGCTCGAGAAAAGAAGC-CCACCCGCCCACAGCCA-3') ( SEQ ID NO:5 ) containing a linker with XhoI site, and reverse primer (5'-GTCAG-GATCCTTACTTGGAGGCAGTCATGA-3') ( SEQ ID NO:6 ) containing a linker with BamHI site, respectively, and liver cDNA (Invitrogen) as template. After purification with QIAquick PCR Kit according to manufactured instruction, linkers digested with Xho1 and BamHI enzymes and native endostatin was ligated into pGEM-T vector (Promega) and the clone of recombinant construct Y-endo-pGEM-T that contains native endostatin was selected. The integrity and accuracy of the desired DNA sequence was confirmed. The native endostatin was excised with XhoI/ NotI and ligated to pPIC9 plasmid. The resulting expression plasmid Y-endo-pPIC9 was transformed into GS115 (Invitrogen) by electroporation. Positive expression clones were selected based on manufacturer's instructions.

Figure 4:
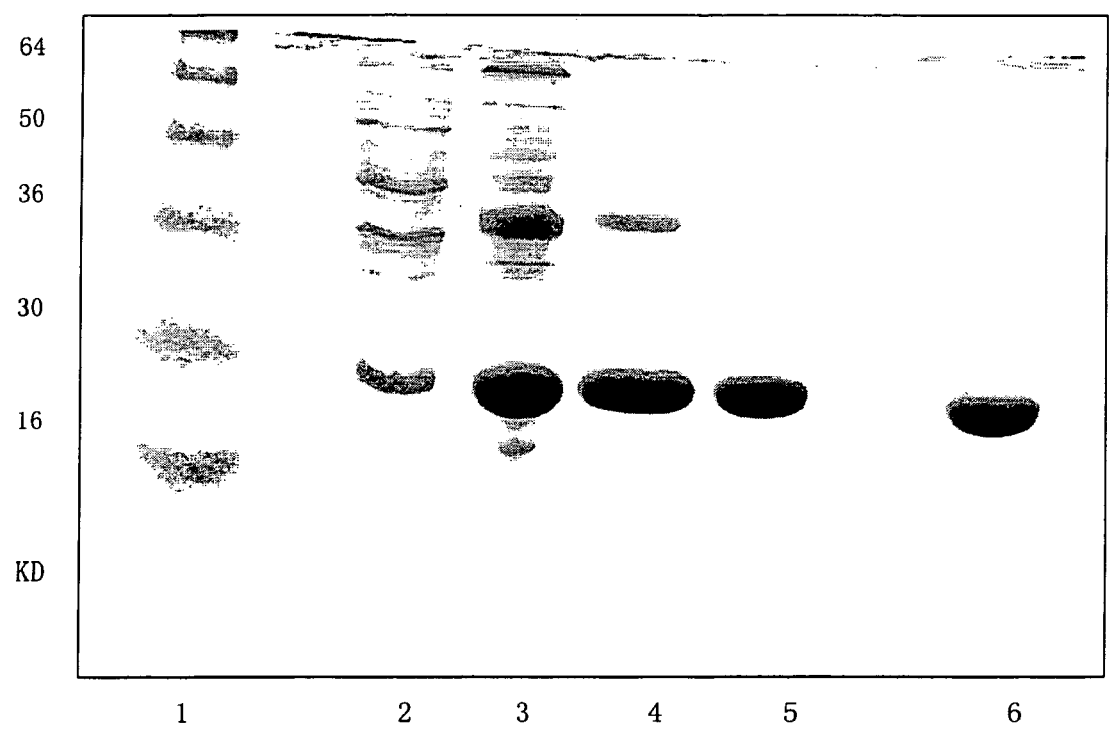
FIG. 4 shows the SDS-PAGE analysis of the yeast expressed, native rhEndostatin during purification. Lane 1: molecular weight marker; Lane 2: supernatant of cell culture; Lane 3: native rhEndostatin after saturated ammonium sulfate precipitation and dialysis; Lane 4: native rhEndostatin after Q-FF chromatography purification; Lane 5: native rhEndostatin after SP-FF chromatography purification, under reducing condition; lane 6: native rhEndostatin after SP-FF chromatography purification, under oxidizing condition.
Figure 5:
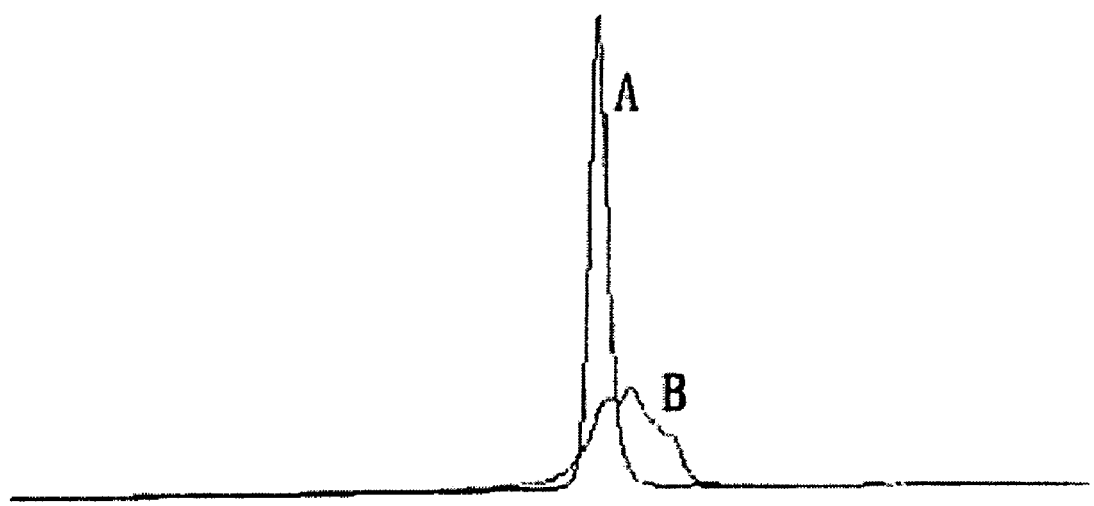
FIG. 5 shows HPLC comparative analysis between purified N-terminal modified rhEndostatin (A) and purified native rhEndostatin (B).

Then Y-endo-GS115 was inoculated in BM-GY media and grown under 30□, shaking at 250 rpm. After about 2 days until the $OD_{600}$ was about 18, yeast cells were harvested by centrifugation. 300 ml of BMMY was added together with methanol (1%) and continued shaking for about another 4 days. After filtration, the supernatant from fermentation broth was added with ammonium sulphate and dialyzed extensively against glycine-HCl (pH 8.5) buffer. Purification was performed with BPG300/500 chromatography columns (Pharmacia), and anion and cation exchange chromatography were performed, respectively. Upon these two steps of purification, the obtained recombinant native endostatin was more than 95% pure (see FIG. 4). Purity of the purified Y-endo was analyzed with RP-HPLC and compared with EH-Endo. Though Y-endo shows one band on SDS-PAGE electrophoresis, it has multiple peaks in RP-HPLC (FIG. 5). This suggests that the high expression level of endostatin in *Pichia pastoris* yeast host might lead to some incorrectly folded protein, or alternatively, some protein has missing amino acids at one of the ends.

Example 4

Evidence for the Renaturation of the N-terminal Modified rhEndostatin

After refolding treatment, the *E. coli* system expressed N-terminal modified rhEndostatin not only became soluble from insoluble under physiological conditions (pH 7.4), it also manifested corresponding changes in molecular behaviors and physical and chemical properties under RP-HPLC, oxidating and reducing gel electrophoresis, ELISA, disulphide bonding analysis, circular dichroism (CD) spectrum, fluorescence spectroscopy, CAM and endothelial migration assay. Thereby, it is concluded that the protein has been refolded in accordance with these testing or experimental data.

(1) RP-HPLC Analysis

Under the proper conditions, the in vitro refolding of purified, denatured proteins to achieve the native secondary and tertiary structure is a spontaneous process. In the unfolded state the hydrophobic residues which are normally found buried in the interior of a protein are more exposed to the polar aqueous environment. Therefore, protein refolding process often manifests as non-polar amino acids getting buried inside from outside of the protein molecule and polar amino acids facing outside. Reverse high pressure liquid chromatography (RP-HPLC) separates and purifies materials based their polar and non-polar properties. Thus it is possible to judge whether protein is refolded based on hydrophilicity and solubility improvement, and retention time of molecules in chromatography columns in RP-HPLC analysis.

With 40–80% acetonitrile gradient, C18 column was used to fractionate and elute proteins to be analyzed. After elution, the retention time of EH-endo molecule before and after refolding on RP-HPLC was tested. The result is shown in FIG. 6.

FIG. 6 shows that the retention time of refolded EH-endo shortened to 11.441 from 12.704 minutes. This result indicates that the refolded protein has increased amount of polar amino acids on the surface and this leads to the improvement of hydrophilicity and solubility.

(2) SDS-PAGE Analysis

The three dimensional nature of protein conformation often brings into proximity amino acid residues that are not normally close to each other based on the direct sequence of the polypeptide chain. The functional form of a protein is generally a modestly stable conformation held together by a combination of cysteine disulfide bonds, ionic bonds, hydrogen bonds, and hydrophobic and Van der Waals interactions. In general, structure of unfolded protein is relatively loose and the effect of disulphide bond on the molecular volume is relatively smaller. So in SDS-PAGE oxidative-reductive electrophoresis analysis, they show almost exactly the same migration rate with or without disulphide bond. Refolded protein, however, has more compact spatial structure and the effect of disulphide bond on molecular volume is much increased. Therefore, they show a distinctive mobility in 12–15% SDS-PAGE oxidative-reductive electrophoresis in the case of presence or absence of S-S bond.

Figure 7:
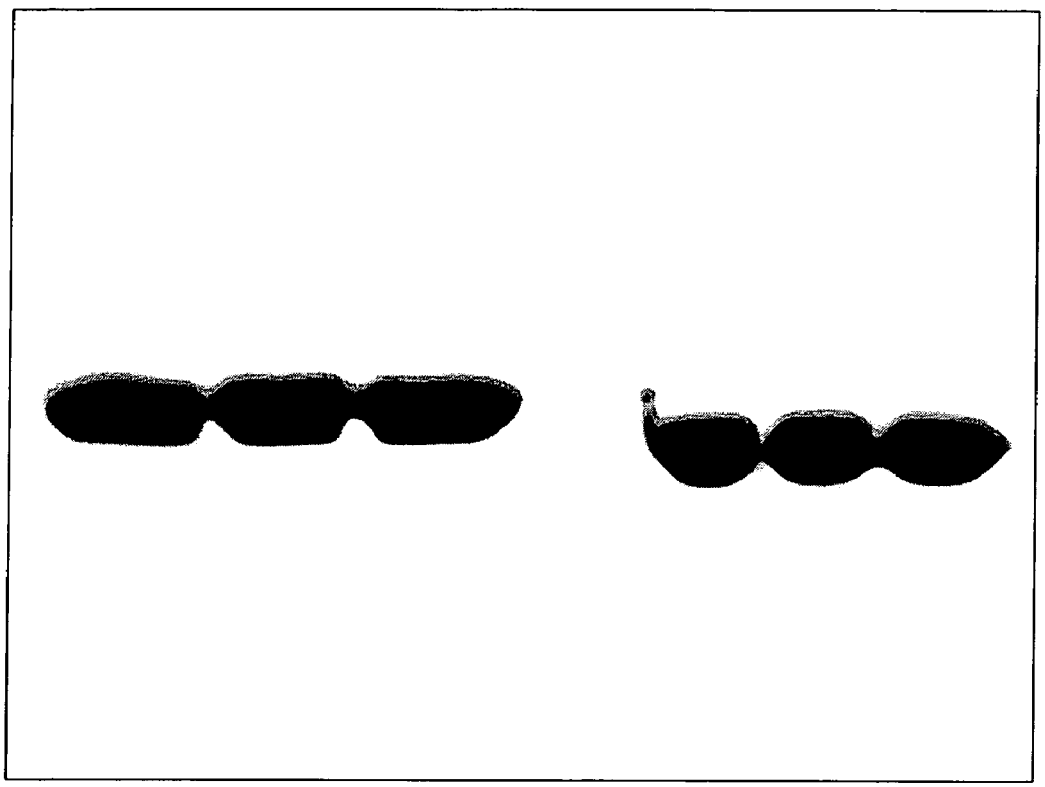
FIG. 7 shows the SDS-PAGE analysis of the N-terminal modified rhEndostatin after refolding under reductive/oxidative conditions. Lanes 1 to 3 and 4 to 6 are reductive and oxidative electrophoresis, respectively.

As shown in FIG. 7, refolded EH-endo shows greater mobility in oxidative gel electrophoresis than that in reductive electrophoresis. This result indicated that refolded protein displays more compact three-dimensional structure than unrefolded one.

(3) ELISA

Antigen-antibody immunological recognition is in fact the reaction between antigen determinant and antibody in a specific spatial environment. Proteins exihibit different spatial structure before and after refolding and show different antibody binding properties. So it is possible to test whether protein has undergone refolding change by means of specific antigen-antibody reactions.

ACCUCYTE immunological analysis (EIA) kit (Cytimmune Science Inc., USA) was used to test the antibody binding ability and characteristics of rhEndostatin protein in order to judge structural change of the protein before and after refolding. Because antibodies used in the kit are polyclonal antibodies specific for yeast produced native endostatin, and because similar curve and slope were observed when EH-endo was tested against such an antibody (FIG. 8), it can be concluded that these two antigens share a similarity in structure.

FIG. 8 also shows that unrefolded EH-endo is not significantly reactive with the antibody provided in the kit, but the refolded EH-endo is reactive with the same antibody. Thus it is concluded that EH-endo protein produced some subtle structural changes during refolding process.

(4) Disulphide Bond Analysis

Correct disulphide bonding is an important criteria to determine whether a protein has restored its native spatial conformation. Thus it is also one of the basics to determine whether a protein is refolded after denaturation. Because protein hydrolases only digest the peptide bond between amino acid residues in a protein and do not break up any intra-molecular disulphide bond, it is possible to use various proteinases to hydrolyze protein and then determine disulphide bonding by mass spectroscopy analysis based on the sizes of the hydrolyzed fragments.

For this purpose, first N-terminal modified endostatin is hydrolyzed with trypsin under non-reducing condition. rhEndostatin contains four cysteines, and 1 and 4, 2 and 3 of these cysteines form a pair of disulphide bonds, respectively (Hohenester E. et al., 1999, EMBO, 17, 1656–1664).

In the following sequence of rhEdostatin, a single letter amino acid abbreviation is used with the cysteine residues given in superscript number.

GGSHHHHHHSHRDFQPVLHLVALNSPSGGMRGIRGADFQC(1)FQQARAVGLAGTFRAF

LSSRLGDLYIVRRADRAAVPIVNLKDELLFPSWEALFSGSEGPLKPG

ARIFSFDGKDVLRHPHPTWPQKSVWHGSDPNGRRLTESYC(2)ETRRTEAPSATG

QASSLLGGRLLGQSAASC(3)HHAYIVLC(4)IENSFMTASK (SEQ ID NO. 7)

Thus, upon trypsin digestion endostatin under non-reducing condition should produce a 5450.19 Dalton peptide as shown below:

| | | |
|---|---|---|
| GADFQC(1)FGGAR | | (SEQ ID NO. 8) |
| LLGQSAASC(3)HHAYIVLC(4)IENSFMTASK | | (SEQ ID NO. 9) |
| LTESYC(2)ETWR | | (SEQ ID NO. 10) |

Figure 9:
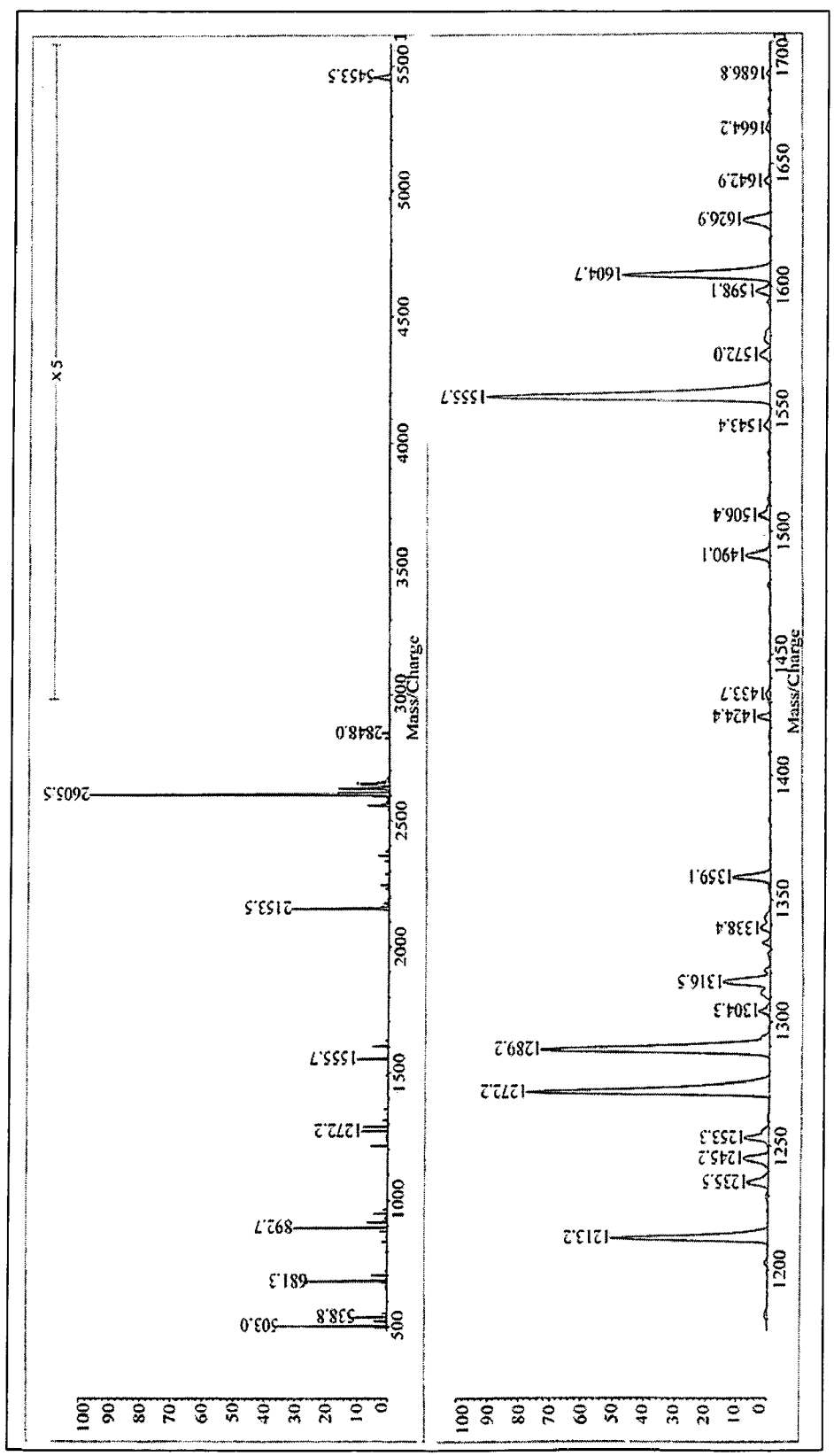
FIG. 9 is the MALDI-TOF-MS mass spectrum analysis of an N-terminal modified rhEndostatin upon non-reducing trypsin hydrolysis.

Then, the resulting hydrolyzed product was subjected to mass spectrum analysis, and the corresponding absorption peak was found in the map (FIG. 9).

Then chymotrypsin, which recognizes different site, was used to repeat the above experiment to obtain more information about the involved disulphide bonding. These experiments demonstrate that the disulphide bonds in the renatured products are indeed formed between cysteine 1 and 4 or 2 and 3.

(5) Circular Dichroism (CD) Analysis

Presently circular dichroism spectra can be measured in dichrograghs with spectropolarimetric apparatus, which after refitting of its optical system can be used for measurement of other optical properties such as optical rotation and/or absorption on a tested substance as well.

Figure 10:
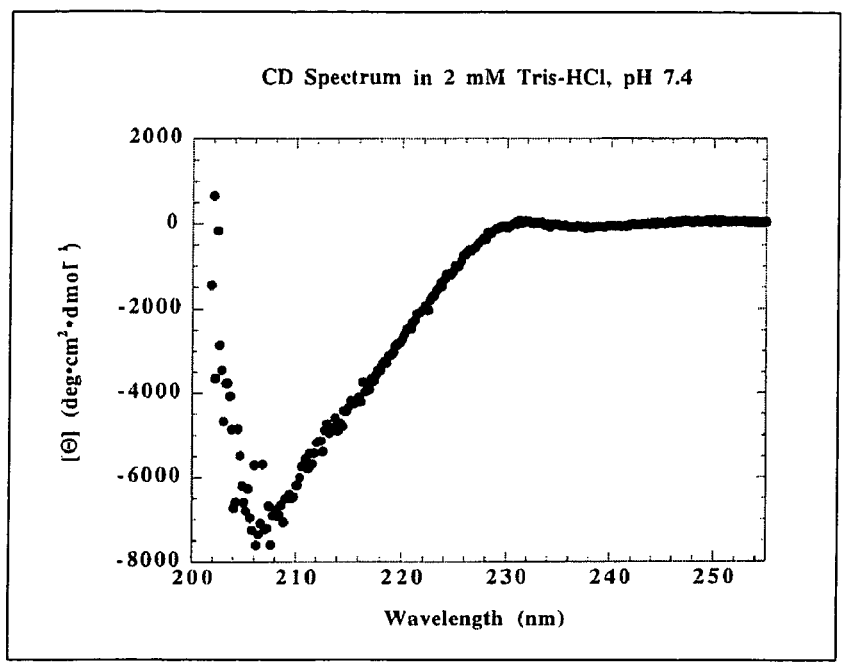
FIG. 10 is the circular dichroism (CD) analysis of an N-terminal modified rhEndostatin after refolding.

For the purpose of the invention, circular dichroism analysis (CD) is used to determine the secondary structure of a protein sample. Circular dichroism spectrophotometric analysis of rhEndostatin of the invention revealed a secondary structure indistinguishable from the wild type. It can be seen from FIG. 10 that N-terminal modified endostatin shows mainly beta-sheet structure and has a minor bending at 222 nm (alpha helix) upon refolding treatment. These CD properties of the refolded endostatin are consistent with previous results reported by Hohenester etc. (Hohenester E. et al., 1999, EMBO, 17, 1656–1664).

(6) Fluorescence Spectrum Analysis

Fluorescence spectrophotometry is used for detection and quantification of analytes in a test sample by measuring the intensity of light emitted by the analytes at various wavelengths, following irradiation by incident light at different wavelengths. Fluorescence is proportional to the number of molecules and compactness of molecular structure of analyte in the irradiated sample.

Figure 11:
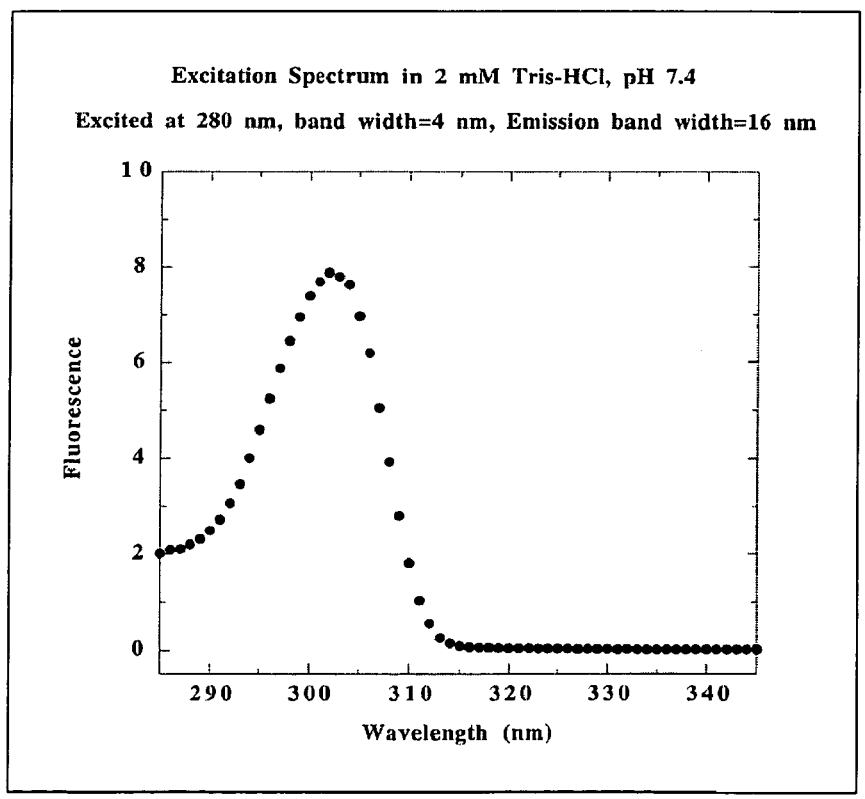
FIG. 11 shows fluorescence analysis of an N-terminal modified rhEndostatin after refolding.

Fluorescence emission spectrum (excited at 280 nm) as shown in FIG. 11 was obtained after fluorescence analysis of the refolded N-terminal modified endostatin (EH-endo). From the fluorescence emission spectrum as shown in FIG. 11, it can be seen that maximum fluorescence emission of the N-terminal modified endostatin is at 320 m, indicating that the refolded EH-endo has relatively condense structure.

(7) In vitro Activity Analysis

In vitro activity analysis is the direct proof of protein renaturation. Endothelial cell line unique to the lab were used to determine activity change for the N-terminal modified endostatin before and after refolding by chick embryo chorioallantoic membrane assay (CAM, see MAI Nguyen et al., Microvascular research 47, 31–40, 1994) and endothelial cell migration inhibition assays. The results are shown in FIGS. 12 and 13.

These results clearly show that the refolded EH-endo according to this invention exhibited a better inhibitory activity on capillary endothelial cell migration and proliferation.

Example 5

Stability In vitro Comparison Between the Modified Endostatin of the Invention and Yeast Produced Endostatin N-terminal modified endostatin produced in example 1 and 2 (EH-endo) and yeast produced native human endostatin (Y-endo) were extensively dialyzed against glycine/HCl buffer (50 mM, pH8.0) and protein concentration was adjusted to about 1 mg/ml, and EDTA (10 mM) was added to the resulted dialyzed solution to remove metal ions including $Zn^{2+}$. After treatment as above, these two kinds of endostatin having different structures and from different sources were divided separately into two parts with or without added ZnSO4, and the resulting four samples were designated as EH-endo+Zn, EH-endo−Zn, Y-endo+Zn and Y-endo−Zn, respectively. These four samples were incubated at 25° C., 37° C. and 60° C. respectively for 15 days. Then samples were taken to determine and analyze their storage stability by SDS-polyacrylamide gel electrophoresis. The result is shown in FIG. 14.

Figure 14:
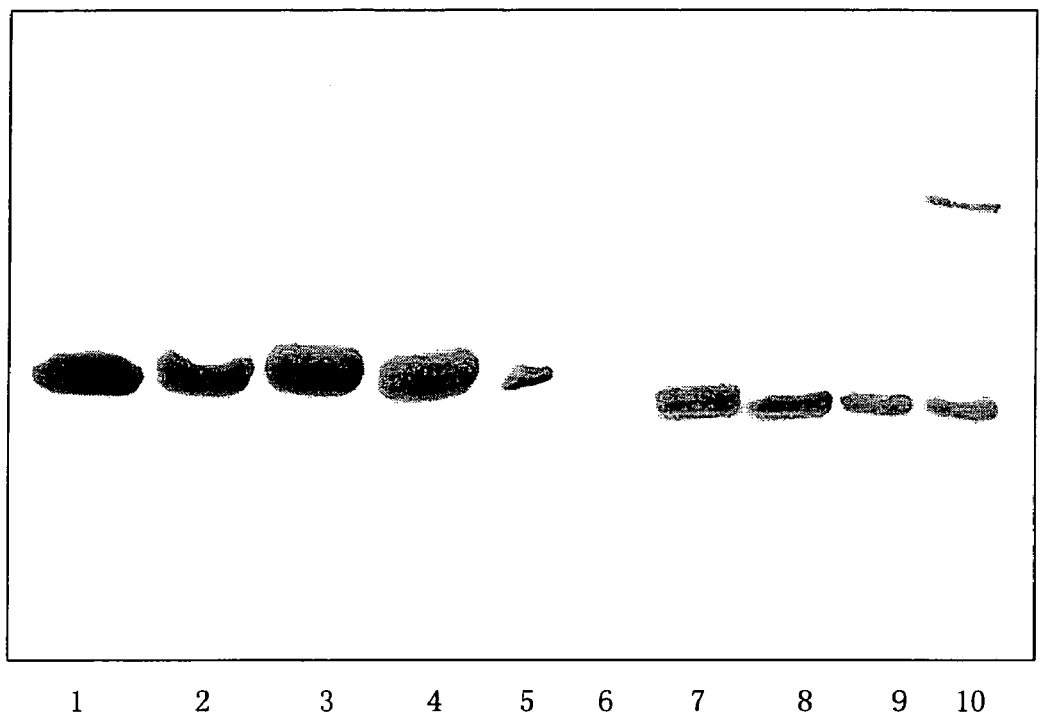
FIG. 14 shows the effect on in vitro storage stability of an N-terminal modified human recombinant endostatin (EH-endo) and native recombinant human endostatin (Y-endo), with or without different concentrations of extra zinc ion ($Zn^{2+}$) addition. SDS-PAGE analysis was performed at different temperatures after 14 days of storage. Lane 1: 25° C., EH-endo with extra $Zn^{2+}$; Lane 2: 25° C., EH-endo without $Zn^{2+}$; Lane 3: 37° C., EH-endo with extra $Zn^{2+}$; Lane 4: 37° C., EH-endo without extra $Zn^{2+}$; Lane 5: 60° C., EH-endo with extra $Zn^{2+}$; Lane 6: 60° C., EH-endo without extra $Zn^{2+}$; Lane 7: 25° C., Y-endo with $Zn^{2+}$; Lane 8: 25° C., Y-endo without extra $Zn^{2+}$; Lane 9: 37° C., Y-endo with extra $Zn^{2+}$; and Lane 10: 37° C., Y-endo without extra $Zn^{2+}$.

As shown in FIG. 14, EH-endo of the invention had no obvious change in protein migration pattern after 15 days of 37° C. incubation in the absence of $Zn^{2+}$. After 15 days of incubation at 60° C., sample with $Zn^{2+}$ added still had minor amount of EH-endo monomer. However, Y-endo protein stored under 37° C. mostly formed multimer (FIG. 14), and Y-endo protein almost all precipitated out after 15 days of incubation at 60° C. in the presence of zinc ion. Thus it is believed that H-endo of the invention has better in vitro stability than yeast-produced native human endostatin in the presence of zinc ion.

Example 6

Stability In vitro Assay of the Modified Recombinant Human Endostatin

In this example, an Enzyme Linked Immunoassay (ELISA) is used to perform in vitro stability testing on human endostatin having different structures produced in example 1–2 and example 3, and analyze the effect of different structures on biological properties of these proteins.

Figure 15:
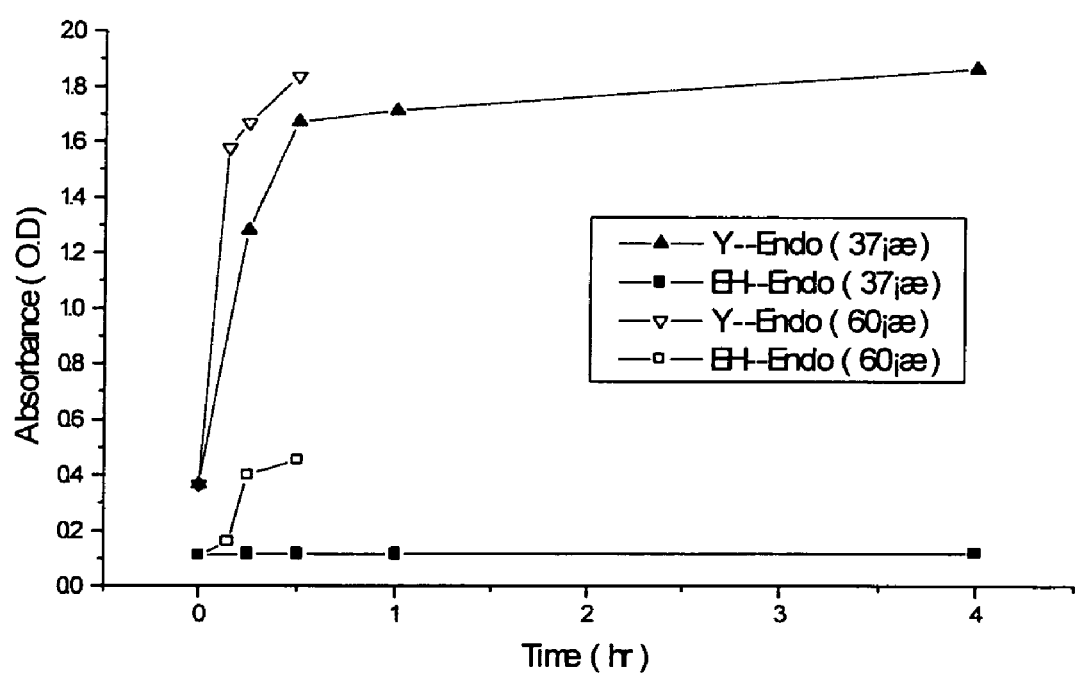
FIG. 15 shows the in vitro stability comparison between rhEndostatin with N-terminal modification of the present invention and native rhEndostatin. Enzyme Linked Immunoassay (ELISA) was used to determine the antibody binding activity of the two products after 0.5–4 hours storage at different temperatures.

First, a commercially available ACCUCYTE Human Endostatin immunological analysis kit was used in ELISA to detect the specific interaction between the human endostatin antibody and the modified rhEndostatin according to the present invention or native human endostatin. From the results as shown in FIG. 15, it can be seen that the two kinds of endostatin having different structures have nearly identical slopes in the antibody binding curves. It is worthy of attention that because the antibody used is made against antigen which is yeast-produced native human endostatin, it seems the antibody has better sensitivity against the latter antigen.

It is generally believed that antigen-antibody recognition reaction is reaction of the antibody against multiple spatial groups of a specific antigen. If an antigen protein has change in spatial structure, this antigen protein will show corresponding change in immunological binding ability and activity with its specific antibody. Thus it is possible to determine the structural change of a specific antigen (or antibody) by means of the specific antigen-antibody binding ability and its strength.

Using a suitable buffer (30 mM NaAc, 5 mM ZnSO4, pH 5.5), concentration of samples was adjusted to 1 mg/ml. The resulting solutions were incubated at 37° C., 60° C. for different length of time respectively and then diluted to appropriate concentration (62.5 ng/ml), and antibody binding activity of these proteins was determined with ELISA. The result is shown in FIG. 15.

It is can be seen from the data as shown in FIG. 15, after 37° C. and 60° C. heat treatment for 30' to 4 hours, the N-terminal modified human endostatin of this invention still showed a good antibody binding activity in ELISA experiments. In contrast, yeast-produced native human endostatin displayed dramatic decrease in antibody binding activity. It is proposed that the additional sequence of the endostatin contributed improving the stability of the molecular structure.

Example 7

Pharmacokinetics Study of the N-terminal Modified rhEndostatin of the Present Invention Nine Cynomolgus monkeys were fed with standard feed for one week and divided into three groups. The three animals in the first group were injected intravenously in the hind legs respectively with three dosages of EH-endo as described above: 1.5, 4.5, and 12.5 mg/kg. The three animals in the second group received subcutaneous injection of EH-endo at dosage of 1.5 mg/kg. The three animals in the third group received daily i.v. injection of 1.5 mg/kg in the hind legs for 7 days. Blood samples were taken at different time points from all animals in the three groups before and after the first and the last injections. After serum separation, the commercial available ACCUCYTE immunological analysis (EIA) kit (Cytimmune Science Inc., USA) was used according to recommended instructions in its accompanying brochure to determine the EH-endo concentration in the serum. After treatment of the experimental data with Origin software (Microcal Co), various pharmacokinetic data were calculated with 3P97 software by linear compartment model and by linear regression equation. Results are shown in table 1 and FIG. 16.

In table 1, AUC, the areas under the concentration-time curve, was calculated by the trapezoidal rule. $AUC_{(0-inf)}$: The area under the curve from time 0 to infinite. $AUC_{(0-z)}$: the area under the curve from time 0 to last time point of measurement. The standard error for each value is shown, and Vc is the volume of distribution of the central compartment; $T_{1/2}$ is half-life of the rhEndostatin protein; $t_{1/2}\alpha$ is initial half-life; $t_{1/2}\beta$ is terminal half-life; Vss is the steady state volume of distribution; Cl is the clearance; MRT is the total body mean residence time; F is bioavailability; Tmax is time to maximum concentration, and Cmax is maximum plasma concentraton.

animals in the third group increased from 22237 ng.h/ml before the drug application to 49609 ng.h/ml after 7 days of administration, thereby calculating the storage factor as 2.3.

Figure 16:
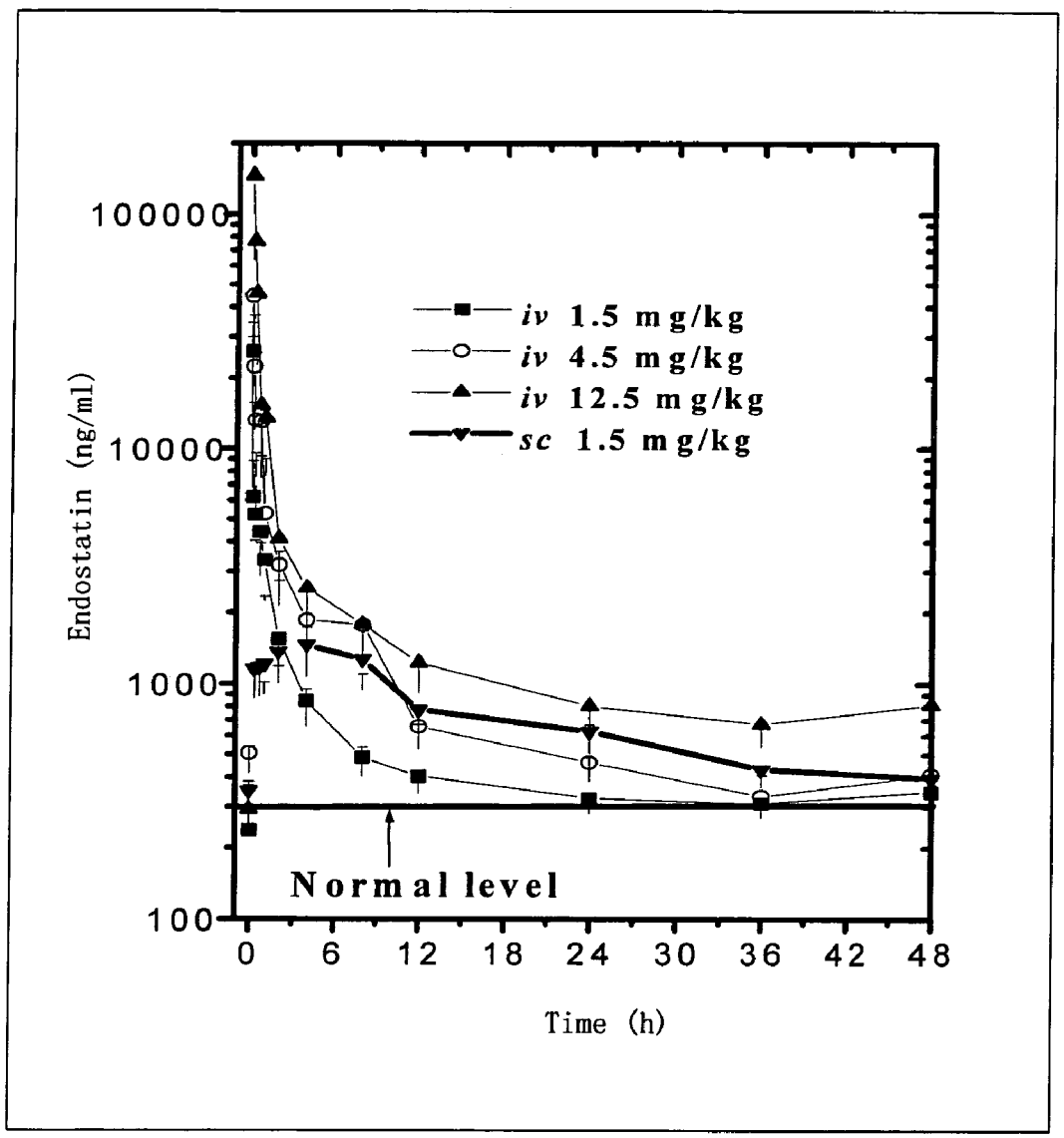
FIG. 16 shows the curve of serum antigen concentration vs time determined by Enzyme Immunological Assay (EIA), after single intravenous or subcutaneous injection of various dosages of N-terminal modified rhEndostatin according to the present invention.

Compared to yeast-produced native endostatin as described by Kim et al. (Kim Lee Sim B. et al. Angiogenesis 3:41–51, 1999), under all conditions with the same dosage (12.5 mg/kg) the modified rhEndostatin of this invention had four times longer terminal half-life (FIG. 16). The serum drug concentration-the total area under the time curve $AUC_{(0-inf)}$ of the modified rhEndostatin of this invention was 6 times of the former (table 1); Though the clearance rate (CITB) of both were basically the same, the apparent distribution volume VB of the modified endostatin according to the present invention was about 1/100 of yeast produced native endostatin.

The above pharmacokinetics experimental results clearly show that compared to yeast produced native human endostatin the modified rhEndostatin of this invention has better in vivo metabolic stability.

TABLE 1

Pharmacokinetics parameters of N-terminal modified rhEndostatin in Cynomolgus monkeys

| parameters | unit | i.v. 1.5 mg/kg | i.v. 4.5 mg/kg | i.v. 13.5 mg/kg | s.c. 1.5 mg/kg |
|---|---|---|---|---|---|
| | | Compartment model | | | |
| $V_C$ | $L \cdot kg^{-1}$ | 0.030 ± 0.019 | 0.082 ± 0.045 | 0.078 ± 0.019*** | 0.078 ± 0.019*** |
| $t_{1/2}$ ka | h | — | — | — | 0.342 ± 0.141 |
| $t_{1/2} \lambda_1$ | h | 0.0274 ± 0.0155 | 0.0434 ± 0.0307 | 0.104 ± 0.042*# | — |
| $t_{1/2} \lambda_2$ | h | 0.798 ± 0.285 | 0.493 ± 0.353 | 0.76 ± 0.51 | 1.87 ± 2.02 |
| $t_{1/2} \lambda_3$ | h | 8.66 ± 8.46 | 3.11 ± 1.45 | 20.5 ± 14.7 | 8.3 ± 3.1 |
| $k_{12}$ | $h^{-1}$ | 21.0 ± 13.7 | 10.6 ± 7.2 | 6.4 ± 5.9 | 0.118 ± 0.101 |
| $k_{21}$ | $h^{-1}$ | 3.48 ± 0.88 | 8.5 ± 3.6 | 2.49 ± 2.39 | 0.88 ± 1.16 |
| $k_{13}$ | $h^{-1}$ | 3.42 ± 4.58 | 1.42 ± 1.12 | 1.25 ± 0.64 | — |
| $k_{31}$ | $h^{-1}$ | 0.237 ± 0.208 | 0.45 ± 0.09 | 0.088 ± 0.060 | — |
| $k_{10}$ | $h^{-1}$ | 5.53 ± 3.58 | 2.51 ± 1.67 | 2.26 ± 0.72 | 0.130 ± 0.048 |
| | | Non-compartment model | | | |
| $T_{max}$ | h | — | — | — | 1.1 ± 0.8 |
| $C_{max}$ | $ng \cdot ml^{-1}$ | — | — | — | 1292 ± 449 |
| $AUC_{0-\infty}$ | $ng \cdot h \cdot ml^{-1}$ | 15384 ± 5081 | 33377 ± 7284* | 93408 ± 24520* | 10751 ± 3561 |
| $MRT_{0-\infty}$ | h | 3.58 ± 0.88 | 2.71 ± 1.46 | 9.2 ± 2.3* | 9.3 ± 1.7 |
| $AUC_{0-Z}$ | $ng \cdot h \cdot ml^{-1}$ | 14188 ± 5498 | 32357 ± 5830* | 85317 ± 20841* | 9880 ± 3825 |
| CL | $L \cdot h^{-1} \cdot kg^{-1}$ | 0.105 ± 0.033 | 0.046 ± 0.010 | 0.017 ± 0.004* | 0.149 ± 0.045 |
| $V_{ss}$ | $L \cdot kg^{-1}$ | 0.392 ± 0.218 | 0.116 ± 0.037 | 0.148 ± 0.013 | 1.422 ± 0.565 |
| F | % | — | — | — | 70 |

It can be seen from the data as shown in table 1 and FIG. 16 that, after intravenous injection of 1.5, 4.5, 12.5 mg/kg modified rhEndostatin of this invention all three animals in the first group showed rapid decrease in serum drug concentration according to three phase model, with half-life at 1.6 minute, 2.6 minutes and 6.2 minutes; terminal phase elimination half-life at 8.66 hours, 3.11 hours, and 20.5 hours respectively; Serum drug concentration—the total area under time curve $AUC_{(0-inf)}$ was 15384, 33377 and 93408 ng.h/ml, respectively; The whole body clearance rate CLs was 0.139, 0.047 and 0.017 L/h/kg, respectively. After subcutaneous injection of 1.5 mg/kg modified rhendostatin of this invention, Tmax of all three animals of the second group was 1.1±0.8 h; Cmax was 1292+−449 ng/ml; AUC is 10751 ng.h/ml; biological availability was 70%. After 7 days of continuous administration of 1.5 mg/kg of the modified rhEndostatin of this invention, the AUC value of all three Example 8

Comparison of Tumor Inhibitory Effects Between Endostatin with Additional N-terminal Sequence of this Invention and Native Endostatin Inhibitory Effect on Growth of Lewis Primary Lung Tumor in Mice Lewis lung tumor cells (LLC-LM) were grown until log phase in DMEM media containing 10% calf serum, treated with trypsin (0.25%) to digest cell monolayer, and then LLC-LM cells were harvested and made into $1 \times 10^7$ cells/ml suspension. 0.1 ml of cell suspension was inoculated subcutaneously in between the T-bones in C57BL/6J mice. When tumor grew to about 1–1.5 cm$^3$ after 2 weeks, animals were sacrificed and tumor tissues were separated sterilely and made into tumor cell suspension ($10^6$ cell/ml). This cell suspension was used to inoculate 15 C57BL/6J mouse, each received 0.1 ml subcutaneously. Nine days afterwards, tumor-bearing animals were randomly divided into three groups when tumors grew to about 100–300 mm$^3$, with 5 animals per group. The first group (positive control) received 100 mg/kg yeast produced native human endostatin on the shaved dorsal region; the second group (experimental group) received the N-terminal modified rhEndostatin of this invention (10 mg/kg); the third group (blank control) received equal volume of PBS. After 13 days of continuous administration, implanted tumor sizes were measured and tumor volumes were calculated according to formula 0.5×a×b$^2$ (a and b represents, respectively, the long and short diameters of the tumor), and tumor inhibition of the drugs were calculated based on the ratio between groups that received drugs vs the group that received no drugs. The result is shown in FIG. 17.

Figure 17:
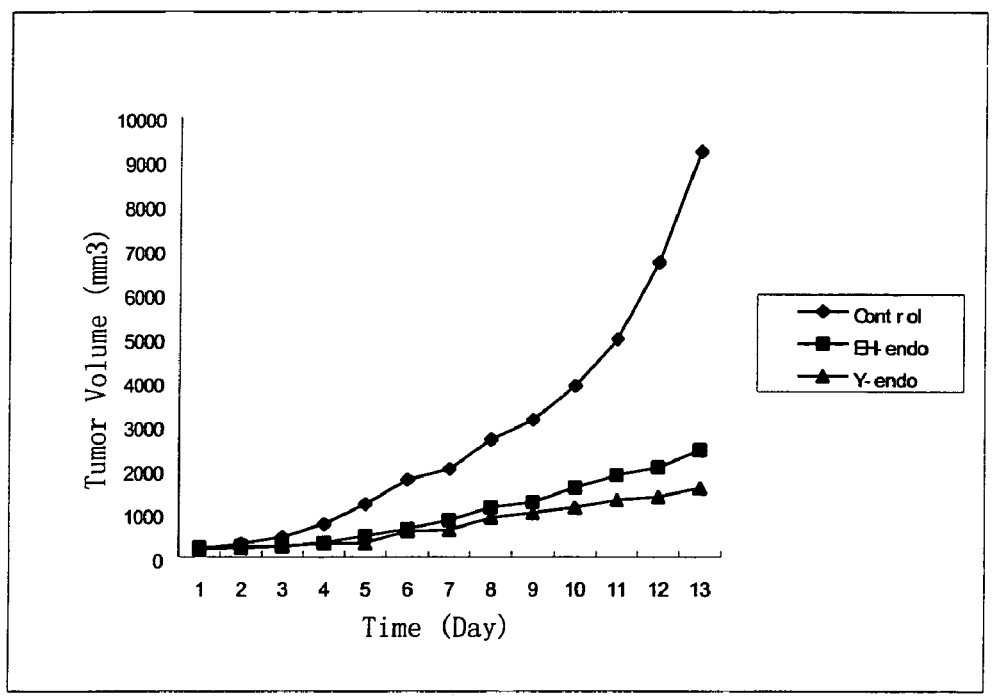
FIG. 17 shows the inhibitory effects of N-terminal modified and native rhEndostatin on the growth of Lewis primary cancer.

It can be seen from the results as shown in FIG. 17 that the N-terminal modified rhEndostatin of this invention has similar tumor inhibitory effect (73.5%) as that of yeast-produced native endostatin (82.9%). However, to achieve such a basically similar tumor inhibitory effects, modified endostatin having increased biological activity can be used at a much lower dosage (about 1/10 of the other).

(1) Inhibitory Effect on the Growth of Human Hepatoma SMMC-7721 in Mice

Human hepatocarcinoma SMMC-7721 cells were grown in DMEM media that contains 10% calf serum to log phase, and cells were digested with 0.25% trypsin, harvested and made into single cell suspension in saline. Then this cell line is inoculated subcutaneously in nude mouse (15) at the rate of 5×10$^6$ cell/each mice. After the inoculants formed transplanted tumors, 3 more generations were passaged in nude mice. Fast growing tumor tissues were removed surgically, cut into 1.5 mm$^3$ pieces and sterilely implanted into the right flank of nude mice. When tumor reaches the size of 100–200 mm$^3$, animals were randomly divided into three groups, with 5 animals in each group. The first group (positive control) receives yeast-produced native rhEdostatin with 3 mg/kg daily i.v. injection; The second group (experimental) received the modified rhEndostatin of the present invention with 3 mg/kg daily i.v. injection. The third group (negative control) received equal volume of saline. After 13 days of continuous administration, diameter of transplanted tumor was measured and tumor volume was calculated based on 0.5×a×b$^2$ (a and b represents the long and short diameters of the tumor, respectively), and then tumor inhibition activities of the drugs were calculated based on the ratio between groups receiving drugs vs the group receiving no drugs. The result is shown in FIG. 18.

Figure 18:
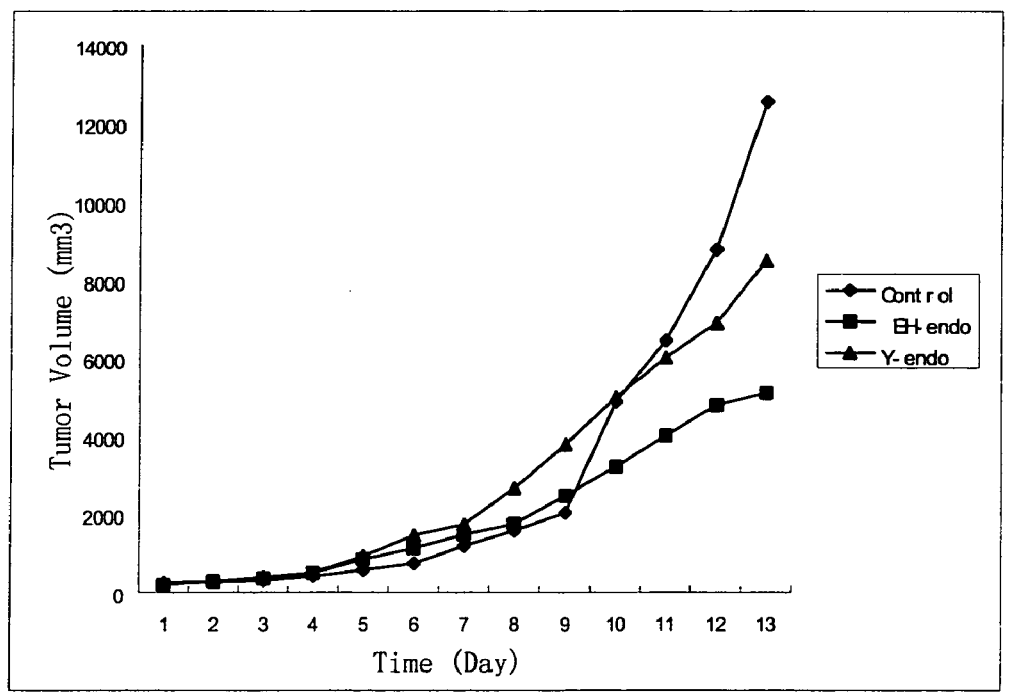
FIG. 18 shows the inhibitory effects of N-terminal modified and native rhEndostatin on the growth of human hepatoma SMMC-7721.

From the results as shown in FIG. 18, it can be seen that after 13 days of injection of the two different kinds of endostatin at the same dosage (3 mg/kg/day), yeast produced native human endostatin has 32.3% inhibition on the growth of human hepatocarcinoma cell while the modified endostatin of this invention has inhibition of about 59.3%. Though the exact mechanism still remains unknown, these experimental results are sufficient to demonstrate that the modified rhEndostatin of this invention has better tumor inhibitory effect compared to yeast produced native human endostatin.

It should be understood that the examples and embodiments described herein are for illustrative purposes only and that various modifications or changes in light thereof will be suggested to persons skilled in the art and are to be included within the spirit and purview of this application

---

What is claimed is:

1. An N-terminal modified recombinant human endostatin protein, wherein said modified endostatin comprises the following general formula:

(Xaa)m(IIis)n-endo wherein Xaa represents any neutral amino acid residue, and m is an integer of 0–4; n is an integer of 2–8, and any two consecutive histidine residues may be separated by one or two non-histidine residues; and -endo represents native endostatin sequence; wherein the first fifteen fourteen --N-terminal amino acids of the modified recombinant human endostatin protein comprise amino acids 2 through 15 of SEQ ID NO:2.

2. A modified recombinant human endostatin according to claim 1, wherein the first fifteen N-terminal amino acids are as listed in SEQ ID NO: 2.

3. A modified recombinant human endostatin according to claim 1, wherein said endostatin protein has a molecular weight of about 21 kDa as determined by reducing gel electrophoresis.

4. A modified recombinant human endostatin according to claim 1, wherein said endostatin protein is produced by DNA recombinant technology in a prokaryotic expression system.

5. A modified recombinant human endostatin according to claim 4, wherein said prokaryotic expression system is *E. coli*.

6. A modified recombinant human endostatin according to claim 4, wherein said endostatin protein is isolated in a refolded form.

7. A modified recombinant human endostatin according to claim 1, wherein said endostatin protein can bind in vivo and in vitro to metal ions, thereby exhibiting an improved stability either in vivo or in vitro as compared to a non-modified human endostatin.

8. A composition comprising an N-terminal modified recombinant human endostatin protein according to claim 1, and one or more pharmaceutically acceptable carriers or excipients.

9. A composition according to claim 8, wherein the first fifteen N-terminal amino acids of said endostatin protein are as listed in SEQ ID NO: 2.

10. A composition according to claim 8, wherein said endostatin protein has a molecular weight of about 21 kDa as determined by reducing gel electrophoresis.

11. A composition according to claim 8, wherein said recombinant human endostatin protein is produced by DNA recombinant technology in prokaryotic expression system.

12. A composition according to claim 8, wherein said recombinant human endostatin protein can bind in vivo and in vitro to the metal ions, and thereby exhibits an improved stability either in vivo or in vitro as compared to a non-modified human endostatin.

* * * * *

UNITED STATES PATENT AND TRADEMARK OFFICE
CERTIFICATE OF CORRECTION

PATENT NO. : 7,078,485 B2
APPLICATION NO. : 10/313638
DATED : July 18, 2006
INVENTOR(S) : Yongzhang Luo, Bing Zhou and Zhuobing Zhang It is certified that error appears in the above-identified patent and that said Letters Patent is hereby corrected as shown below:

Column 1,
Line 9, "have a additional" should read --have an additional--.
Line 37, "267:109931-10934," should read --267:10931-10934,--.

Column 3,
Line 26, "demands huge amount of" should read --demands a huge amount of--.

Column 4,
Line 51, "expressed in prokaryote hosts." should read --expressed in prokaryotic hosts.--.

Column 5,
Lines 8-9, "m is a integer between 0 and 4; n is a integer between 2 and 8," should read
    --m is integer of 0-4; n is integer of 2-8,--.
Line 51, "genesis-related diseases,." should read
    --genesis-related diseases.--.

Column 6,
Line 16, "FIGS. 6A-6B are is RP-HPLC" should read --FIGS. 6A-6B are RP-HPLC--.

Column 7,
Line 15, "(rhendostatin)" should read --(rhEndostatin)--.

Column 9,
Lines 14-15, ", which incorporated herein" should read --, which is incorporated
    herein--.
Lines 22-23, "For the convenience," should read --For convenience,--.

Column 10,
Line 4, "protein expression results." should read
    --and the protein expression is the result.--.
Line 41, "MetGlyGlySerHisHIsHisHisHis" should read
    --MetGlyGlySerHisHisHisHisHis--.

Column 11,
Line 65, "under reducing condition" should read --under reducing conditions--.

Column 12,
Line 42, "Also, Earlier crystal" should read --Also, earlier crystal--.

UNITED STATES PATENT AND TRADEMARK OFFICE
CERTIFICATE OF CORRECTION

PATENT NO.       : 7,078,485 B2
APPLICATION NO.  : 10/313638
DATED            : July 18, 2006
INVENTOR(S)      : Yongzhang Luo, Bing Zhou and Zhuobing Zhang It is certified that error appears in the above-identified patent and that said Letters Patent is hereby corrected as shown below:

Column 13,
Line 24, "for different length of time," should read --for different lengths of time,--.

Column 15,
Line 19, "the required particular size" should read --the required particle size--.
Lines 53-54, "but not antagonize to each other" should read
    --but not antagonistic to each other--.

Column 16,
Line 8, "elongated rhendostatin" should read --elongated rhEndostatin--.

Column 18,
Line 31, "Thereafter, Purified product" should read --Thereafter, purified product--.
Line 51-52, "grown in 37☐ shaker" should read --grown in 37°C shaker--.

Column 19,
Line 10, "purified modified ndostatin." should read --purified modified endostatin.--.
Lines 59-60, "according to manufactured instruction" should read
    --according to manufacturer's instructions--.

Column 20,
Line 4, "grown under 30☐," should read --grown under 30°C,--.

Column 24,
Line 40, "It is can be seen from the data" should read --It can be seen from the data--.
Line 47, "contributed improving the stability" should read
    --contributed to improving the stability--.

UNITED STATES PATENT AND TRADEMARK OFFICE
CERTIFICATE OF CORRECTION

PATENT NO. : 7,078,485 B2
APPLICATION NO. : 10/313638
DATED : July 18, 2006
INVENTOR(S) : Yongzhang Luo, Bing Zhou and Zhuobing Zhang It is certified that error appears in the above-identified patent and that said Letters Patent is hereby corrected as shown below:

Column 29,
Lines 52-53, "wherein the first fifteen fourteen --N-terminal" should read
--wherein the first fifteen N-terminal--.

Signed and Sealed this

Twenty-sixth Day of December, 2006

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial sequence ( N-terminal additional amino acid
      sequence )
<220> FEATURE:
<223> OTHER INFORMATION: N-terminal additional amino acid sequence

<400> SEQUENCE: 1

Met Gly Gly Ser His His His His His
1               5

<210> SEQ ID NO 2
<211> LENGTH: 15
<212> TYPE: PRT
<213> ORGANISM: Artificial sequence
<220> FEATURE:
<223> OTHER INFORMATION: plus N-terminal 9 amino acid sequence of native
      rhEndostatin

<400> SEQUENCE: 2

Met Gly Gly Ser His His His His His Ser His Arg Asp Phe
1               5                   10                  15

<210> SEQ ID NO 3
<211> LENGTH: 33
<212> TYPE: DNA
```

```
<213> ORGANISM: Artificial sequence
<220> FEATURE:
<223> OTHER INFORMATION: artificially synthesized primer sequence

<400> SEQUENCE: 3
catatggggg gttctcatca ccatcaccat cac                                    33

<210> SEQ ID NO 4
<211> LENGTH: 29
<212> TYPE: DNA
<213> ORGANISM: artificial
<220> FEATURE:
<223> OTHER INFORMATION: artificially synthesized primer sequence

<400> SEQUENCE: 4
ctcgagctac ttggaggcag tcatgaagc                                         29

<210> SEQ ID NO 5
<211> LENGTH: 34
<212> TYPE: DNA
<213> ORGANISM: artificial
<220> FEATURE:
<223> OTHER INFORMATION: artificially synthesized primer sequence

<400> SEQUENCE: 5
cgctcgagaa aagaagccca cccgcccaca gcca                                   34

<210> SEQ ID NO 6
<211> LENGTH: 30
<212> TYPE: DNA
<213> ORGANISM: artificial
<220> FEATURE:
<223> OTHER INFORMATION: artificially synthesized primer sequence

<400> SEQUENCE: 6
gtcaggatcc ttacttggag gcagtcatga                                        30
```